US007282598B2

(12) United States Patent
Romanczyk, Jr. et al.

(10) Patent No.: US 7,282,598 B2
(45) Date of Patent: Oct. 16, 2007

(54) SYNTHETIC METHODS FOR PREPARING PROCYANIDIN OLIGOMERS

(75) Inventors: Leo J. Romanczyk, Jr., Hackettstown, NJ (US); Amit Basak, Baltimore, MD (US); Craig A. Townsend, Baltimore, MD (US)

(73) Assignee: Mars, Inc.

( * ) Notice: Subject to any disclaimer, the term of this patent is extended or adjusted under 35 U.S.C. 154(b) by 191 days.

(21) Appl. No.: 10/798,131

(22) Filed: Mar. 11, 2004

(65) Prior Publication Data
US 2004/0176441 A1 Sep. 9, 2004

Related U.S. Application Data

(60) Division of application No. 10/212,973, filed on Aug. 6, 2002, now Pat. No. 6,864,377, and a continuation of application No. 10/212,973, filed on Aug. 6, 2002, now Pat. No. 6,864,377, which is a continuation of application No. 09/292,244, filed on Apr. 15, 1999, now Pat. No. 7,015,338.

(51) Int. Cl.
C07D 311/04 (2006.01)
C07D 311/74 (2006.01)
C07D 311/76 (2006.01)
C07D 313/00 (2006.01)

(52) U.S. Cl. ............... 549/354; 549/355; 549/399; 549/406

(58) Field of Classification Search ........... 549/406, 549/399
See application file for complete search history.

(56) References Cited

U.S. PATENT DOCUMENTS

| 4,255,336 | A |   | 3/1981 | Albert et al. ............ 260/345.2 |
| 4,644,011 | A |   | 2/1987 | Ballenegger et al. ........ 514/456 |
| 5,554,645 | A |   | 9/1996 | Romanczyk, Jr. et al. ... 514/453 |
| 6,156,912 | A |   | 12/2000 | Tuckmantel et al. ......... 549/399 |
| 6,207,842 | B1 |  | 3/2001 | Romanczyk, Jr. et al. ... 549/399 |
| 6,420,572 | B1 |  | 7/2002 | Romanczyk, Jr. et al. ... 549/400 |
| 6,476,241 | B1 |  | 11/2002 | Kozikowski et al. ........ 549/399 |
| 6,528,664 | B2 |  | 3/2003 | Romanczyk et al. ........ 549/400 |
| 6,720,432 | B2 |  | 4/2004 | Kozikowski et al. ........ 549/415 |
| 6,864,377 | B2 | * | 3/2005 | Romanczyk et al. ........ 549/354 |
| 7,067,679 | B2 |  | 6/2006 | Kozikowski et al. |
| 7,126,014 | B2 |  | 10/2006 | Kozikowski et al. |
| 2003/0114691 | A1 |   | 6/2003 | Romanczyk et al. ........ 549/354 |
| 2003/0176620 | A1 |   | 9/2003 | Romanczyk et al. .......... 528/86 |

FOREIGN PATENT DOCUMENTS

| DE | EP 0039844 | 11/1978 |
| EP | DE 15 18 003.7 | 1/1969 |
| EP | 0096 007 | 5/1983 |
| EP | 0216 963 | 4/1987 |
| JP | 58 154 571 A | 9/1983 |
| JP | 06 248677 A | 3/1987 |
| JP | 41 90774 | 11/1990 |
| WO | WO90/13304 | 11/1990 |
| WO | WO97/36597 A | 10/1997 |

OTHER PUBLICATIONS

Kozikowski et al., J. Org. Chem. 2000, vol. 65, pp. 5371-5381.
Balde, A.M. et al. Phytochemistry, vol. 30, No. 12. p. 4129-4135 (1991).
Funayama, M. et al, Biosci, Biotech., 58, (5), 817-821 (1994).
Kolodziej, H., Phytotherapy Research, 9:410-415 (1995).
Nonaka G-I., Chem. Pharm. Bull. 31 (11) 3906-3914 (1983).
Okuda, T. et al, Molecular Structures and Pharmacological activities of Polyphenols—Oligomeric Hydrolyzable Tannins and Others—Presented at the XVIth International Conference of the Groupe Polyphenols, Lisbon, Portugal, Jul 13-16, 1992.
Roux, D.G. et al, Progress in the Chemistry of organic Natural Products 41, p. 47-76 (1982).
Botha, J.J. et al, J. Chem. Soc. Perkin I, 1235-1245 (1980).
Botha, J.J. et al, J. Chem. Soc. Perkin I, 527-533 (1982).
Chu, S.C. et al, J. of Natural Products, 55, (2), 179-183 (1992).
Delcour, J.A. et al, J. Chem. Soc. Perkin Trans I 1711-1717 (1983).
Deschner, E.E. et al, Carcinogenesis, 7, 1193-1196, (1991).
Ferriera, D. et al, Tetrahedron, 48, (10), 1743-1803 (1992).
Foo, L.Y. et al, J. Chem. Soc. Perkin I 1983:1535-1543.
Foo, L.Y. et al, J. Chem. Soc., Commun., 85-86 (Sep. 1984).
Funayama, M. et al, Biosci. Biotech. Biochem., 58, (5), 817-821 (1994).
Ho, C.T., Lee C.Y., and Huang, M.T. Eds., Phenolic Compounds in Foods and Their Effects on Health I. Analysis, Occurrence and Chemistry, ACS Symposium Series 506, American Chemical Society, Washington D.C. (1992).
Hundt, H.K. et al, J. Chem. Soc. Perkin I: 1227-1234 (1981).
Kato, R. et al. Carcinogenesis, 1301-1305 (1983).
Kawamoto, H, et al. Synthetic Communications, 26(3), 531-534 (1996).
Kawamoto, H. et al, Mokazai gakkaishi, 37, (5) 488-493 (1991).
Keough et al, Chem. Ind. (London) 2100-1 (1961). Abstract only.
Khanbabaee, K. et al, Tetrahedron, 53:31, 10725-10732 (1997).
Kiatgrajai P., et al. J. Org. Chem. 47, 2910-2012 (1982).

(Continued)

Primary Examiner—James O. Wilson
Assistant Examiner—Ebenezer Sackey
(74) Attorney, Agent, or Firm—Margaret B. Kelley; Gibbons, P.C.

(57) ABSTRACT

Processes are disclosed for the production of linear and branched procyanidin oligomers having "n" procyanidin monomeric units where n is 2 to 18. The processes include coupling protected, activated monomers with an unprotected monomer to produce a partially protected (4→8) dimer. The dimer is optionally blocked, coupled with an activated protected monomer to produce a partially protected, optionally blocked trimer, and deprotected. The steps can be repeated to produce higher oligomers. Processes are also provided for producing (8→8), (8→6), and (6→6) dimers and doubly branched oligomers. Crystalline 8-bromo tetra-O-benzyl (−)-epicatechin is produced under certain conditions.

13 Claims, No Drawings

OTHER PUBLICATIONS

Kitao et al, *Biosci. Biotech. Biochem.* 59(11), 2167-2169, (1995).
Kozikowski, A, et al. *J. Org. Chem.*, 65, 5371-5381 (2000).
Meyer, S., *J. Org. Chem.*, 59: 7549-7552 (1994).
Newman, R.H., Magnetic Resonance in Chemistry 25:118-124 (1987).
Nonaka G-I., et al. *J. Chem. Soc. Perkin Trans.*, I: p. 2139-2145 (1983).
Pierre. M.C. et al. Tetrahedron Letters 38, (32), 5639-5642 (1997).
Porter, L.J. "Flavans and Proanthocyanidins" from "The Flavonoids" Ed. J.B. Harborne, Chapmen and Hall Ltd., p. 21-62 (1988).
Roux & Ferreira, Fortschritte d. Chemie Org. Naturst., pp. 47-76 (1982).
Roux, D.G. et al, *J. Agric. Food Chem.* 28:216-222 (1980).
Saito, Akiko et al., "Synthetic Studies of Proanthocyanidins. Highly Stereoselective Synthesis of the Catechin Dimer, Procyanidin-B3", Biosci. Bioetechnol. Biochem., 66(8), 1764-1767, 2002.
Steenkamp et al, Tetrahedron letters, 26, (25) 3045-3048 (1985).
Steynberg, P.J. et al, Tetrahedron 54:8153-8158 (1998).
Toshima, K., Tatsuta, K., *Chem. Rev.*, 93, 1503-1531 (1993).
Weinges, K. et al. *Chem. Ber.* 103, 2344-2349 (1970).
Kozikowski et al., "Synthesis of a 4-a-Arylepicatechins", U.S. Appl. No. 11/543,415, filed Oct. 5, 2006.
Kozikowski et al., "Synthesis of Dimeric, Trimeric, Tetrameric, Pentameric, and Higher Oligomeric . . . ", U.S. Appl. No. 11/329,467, filed Jan. 11, 2006 (A.U. 1626).
Kozikowski, et al., "Synthesis of Oligomeric Epicatechin- and Catechin-Derived Procyanidins", U.S. Appl. No. 10/481,729, filed Sep. 15, 2004 (A.U. 1626).
Romanczyk et al., "Processes for the preparation of protected-(+)-catechin and (-)-epicatechin monomers, for coupling . . . ", U.S. Appl. No. 11/169,860, filed Jun. 29,2005 (A.U. 1625).
Delcour, et al., "Synthesis of Condensed Tannins. Part 13. The First 2,3-trans-3,4-cis . . . " J. Chem. Soc. Perkin Trans. I (1985) 669-676.
Foo, et al., "Proanthocyanidins From Lotus Corniculatus" Phytochemistry (1996) 41, No. 2: 617-624.
Kolodziej, "The first 2,3-trans-3,4-cis Procyanidin" Phytochemistry (1985) 24, No. 10: 2460-2462.
Mayer, et al., "Procyanidino-(-)-Epicatechin . . . " Tetrahedron Letters (1996) No. 4: 429-435.
Saito, et al., "Synthetic Studies of Proanthocyanidins. Part 2: Stereoselective gram-scale synthesis . . . " Tetrahedron Letters (2002) 58:7829-7837.
Saito, et al., "Synthetic Studies of Proanthocyanidins. Part 3: Stereoselective 3,4-cis catechin . . . " Tetrahedron Letters (2003) 44:5449-5452.
Viswanadhan et al., "Assessment by Molecular Mechanics of the Preferred Conformations . . . " J. Chem. Soc. Perkin Trans. II (1987) 739-743.
U.S. Appl. No. 09/292,244, filed Apr. 15, 1999, Basak et al.
U.S. Appl. No. 10/658,241, filed Sep. 9, 2003, Kozikowski et al.
U.S. Appl. No. 10/783,801, filed May 28, 2004, Kozikowski et al.
U.S. Appl. No. 10/481,729, filed Dec. 22, 2003, Kozikowski et al.
Tuckmantel, et al., Studies in Polyphenol Chemistry and Bioactivity. 1. Preparation of Building Blocks from (+)-Catechin. Procyanidin Formation. Synthesis of the Cancer Cell Growth Inhibitor, 3-$O$-Galloyl-($2R,3R$)-epicatechin-4β,8-[3-$O$-galloyl-($2R,3R$)-epicatechin], *J. Am. Chem. Soc.*, 1999, 121, 12073-12081.
Kozikowski, et al., "Studies in Polyphenol Chemistry and Bioactivity. 3. [1,2] Stereocontrolled Synthesis of Epicatechin-4α,8-epicatechin, an Unnatural Isomer of the B-Type Procyanidins", *J. Org. Chem.*, 2001, 66, 1287-1296.

* cited by examiner

SYNTHETIC METHODS FOR PREPARING PROCYANIDIN OLIGOMERS

This application is a division and continuation of Ser. No. 10/212,973 filed Aug. 6, 2002, now U.S. Pat. No. 6,864,377 issued Mar. 8, 2005, which is a continuation of Ser. No. 09/292,244 filed Apr. 15, 1999, now U.S. Pat. No. 7,015,338 issued Mar. 21, 2006.

FIELD OF INVENTION

This invention relates to synthetic procyanidin oligomers and methods for making and using the oligomers.

BACKGROUND OF THE INVENTION

Polyphenols are a highly diverse group of compounds (Ferreira, D., Steynberg, J. P., Roux, D. G. and Brandt, E. V., *Tetrahedron*, 48 (10), 1743-1803 (1992)) which widely occur in a variety of plants, some of which enter into the food chain. In some cases they represent an important class of compounds for the human diet. Although some of the polyphenols are considered to be non-nutritive, interest in these compounds has increased because of their possible beneficial effects on health.

For instance, quercetin has been shown to possess anti-carcinogenic activity in experimental animal studies (Decshner, E. E., Ruperto, J., Wong, G. and Newmark, H. L., *Carcinogenesis*, 7, 1193-1196 (1991) and Kato, R., Nakadate, T., Yamamoto, S. and Sugimura, T., *Carcinogenesis*, 4, 1301-1305 (1983)). (+)-Catechin and (−)-epicatechin have been shown to inhibit leukemia virus reverse transcriptase activity (Chu, S.-C., Hsieh, Y.-S. and Lim, J.-Y., *J. of Natural Products*, 55 (2), 179-183, (1992)). Nobatanin (an oligomeric hydrolyzable tannin) has also been shown to possess anti-tumor activity (Okuda, T., Yoshida, T., and Hatano, T., Molecular Structures and Pharmacological Activities of Polyphenols—Oligomeric Hydrolyzable Tannins and Others—Presented at the XVIth International Conference of the Group Polyphenols, Lisbon, Portugal, Jul. 13-16, 1992). Statistical reports have also shown that stomach cancer mortality is significantly lower in the tea-producing districts of Japan. Epigallocatechin gallate has been reported to be the pharmacologically active material in green tea that inhibits mouse skin tumors (Okuda et al., Ibid.). Ellagic acid has also been shown to possess anticarcinogen activity in various animal tumor models (Boukharta, M., Jalbert, G. and Castonguay, A., Efficacy of Ellagitannins and Ellagic Acid as Cancer Chemopreventive Agents—Presented at the XVIth International Conference of the Group Polyphenols, Lisbon, Portugal, Jul. 13-16, 1992). Proanthocyanidin oligomers have been patented by the Kikkoman Corporation for use as antimutagens. The use of phenolic compounds in foods and their modulation of tumor development in experimental animal models has been recently presented at the 202$^{nd}$ National Meeting of the American Chemical Society (Phenolic Compounds in Foods and Their Effects on Health I, Analysis, Occurrence & Chemistry, Ho, C.-T., Lee, C.Y. and Huang, M.-T. editors, ACS Symposium Series 506, American Chemical Society, Washington, D.C. (1992); Phenolic Compounds in Foods and Their Effects on Health II. Antioxidants & Cancer Prevention, Huang, M.-T., Ho, C.-T. and Lee, C.Y. editors, ACS Symposium Series 506, American Chemical Society, Washington, D.C. (1992)).

However, these citations do not relate to cocoa extracts or compounds therefrom or to any methods for preparing such extracts or compounds therefrom, or to any of the uses described in U.S. Pat. No. 5,554,645 issued Sep. 10, 1996 to Romanczyk et al., U.S. Pat. No. 5,712,305 issued Jan. 27, 1998 to Romanczyk et al., and U.S. Pat. No. 5,650,432 issued Jul. 22, 1997 to Walker et al.

Isolation, separation, purification, and identification methods have been established for the recovery of a range of procyanidin oligomers for comparative in vitro and in vivo assessment of biological activities. For instance, anti-cancer activity is elicited by pentameric through decameric procyanidins, but not by monomers through tetrameric compounds. Currently, gram quantities of pure (>95%) pentamer are obtained by time-consuming methods. These methods are not satisfactory for obtaining sufficient quantities of the pentamer for large scale pharmacological and bioavailability studies. Even greater effort is required to obtain multi-gram quantities of higher oligomers (hexamers through decamers) for similar studies since their concentration in the natural product is much less than the pentamer. Additionally, increasing oligomeric size increases structural complexity. Factors such as the chirality of the monomeric units comprising the oligomer at different interflavan linkage sites, dynamic rotational isomerization of the interflavan bonds, conformational states of the pyran ring, and the multiple points of bonding at nucleophilic centers pose efficiency constraints on current analytical methods of separation and purification for subsequent identification.

For instance, previous attempts to couple monomeric units in free phenolic form using mineral acid as the catalyst in aqueous media have met with limited success. The yields were low, the reactions proceeded with poor selectivity, and the oligomers were difficult to isolate. (Stynberg, P. J., Nel, R. J., and Ferreira, D., *Tetrahedron*, 54, 8153-8158 (1998); Botha, J. J., Young, D. A., Ferreira, F., and Roux, D. J. J., *J. Chem. Soc., Perkins Trans.* 1, 1213-1219 (1981)).

Benzylated monomers have been prepared by methods described by Kawamoto, H., Nakatsubo, F. and Murkami K., *Mokuzai Gakkashi*, 37, 741-747 (1991) where benzyl bromide was used in combination with potassium carbonate ($K_2CO_3$), and dimethyl formamide (DMF). The yield, however, was only about 40%. In addition, competing C-benzylation leads to a mixture of products which makes isolation of the target monomer more difficult. Also, partial racemization of (+)-catechin at both the C-2 and C-3 positions was observed (Pierre, M.-C. et al., *Tetrahedron Letters*, 38: 32, 5639-5642 (1997)).

Two primary methods for oxidative functionalization are taught in the literature (Betts, M. J., Brown, B. R. and Shaw, M. R., *J. Chem. Soc., C.* 1178 (1969); Steenkamp, J. A., Ferreira, D. and Roux, D. J., *Tetrahedron Lett.*, 26, 3045-3048 (1985)). In the older method, protected (+)-catechin was treated with lead tetraacetate (LTA) in benzene to produce the 4β-acetoxy derivative which was then successfully hydrolyzed to the 3,4-diol. Flavan-3,4-diols are incipient electrophiles in the biomimmetic synthesis of procyanidins. However, flavan 3,4-diols which have an oxygen functionality at the C-5 position are not available from natural sources and have to be synthesized. Oxidative functionalization of the prochiral benzylic position to form the 3,4-diols thus offers considerable potential in the synthesis of procyanidins. The major drawback of this reaction was a low yield (30-36%) of the acetate during the LTA oxidation. The more recent method of oxidatively functionalizing the C-4 position relies on the use of 2,3-dichloro-5,6-dicyano-1,4-benzoquinone (DDQ). In this method, the protected monomer was treated with DDQ in methanol. This allows introduction of a methoxy group at the C4 position in a stereospecific manner. The yield is about 40-50%.

There are a number of reports on the coupling reaction between monomers and their 3,4-diols in aqueous acid. These methods are unsatisfactory because of low yields, lack of specificity, and difficulty in the purification from aqueous media. Kawamoto, H., Nakatsubo, F. and Murakami, K., *J. of Wood Chem. Tech.*, 9, 35-52 (1989) report the titanium tetrachloride ($TiCl_4$) mediated coupling between 4-hydroxyl tetra-O-benzyl (+)-catechin and 5 equivalents (eq) of tetra-O-benzyl (+)-catechin to produce a 3:2 mixture of 4α→8 and 4β→8 dimers.

Hence, there is a need for synthesis methods which provide large quantities of structurally defined oligomers for in vitro and in vivo assessment. Such synthesis methods can lead to the creation of multiple configurational oligomers, some identical to those found in nature, as well as rare or "unnatural" types. Accordingly, it would be advantageous to develop a versatile synthetic process capable of providing large quantities of any desired procyanidin oligomer.

SUMMARY OF THE INVENTION

A process for the preparation of a partially protected procyanidin dimer is provided. It comprises the steps of:
(a) protecting each phenolic hydroxyl group of a catechin monomer or an epicatechin monomer with a removable protecting group which does not deactivate the A ring of the monomer, wherein the protecting step is carried out in an aprotic solvent;
(b) optionally blocking the C-8 position of the monomer of step (a) with a halo group;
(c) activating the monomer of step (a) or step (b) by introducing an acyloxy group at the C-4 position using a lead (IV) salt of an organic acid; and
(d) catalytically coupling the monomer of step (c) with an unprotected catechin monomer or an unprotected epicatechin monomer to form the dimer.
(e) coupling the activated compound of step (b) with an unprotected procyanidin monomer in the presence of a coupling catalyst to produce the dimer.

A process is also provided for the preparation of a linear procyanidin oligomer having 4→8 linkages. It comprises the steps of:
(a) preparing a partially protected (4→8) procyanidin dimer, where the phenolic hydroxyl groups of the top mer are protected with a removable protecting group which does not deactivate the A ring of the protected mer;
(b) masking the the dimer of step (a) to form a dimer where the phenolic hydroxyl groups of the top mer are protected, where the phenolic hydroxyl groups of the bottom mer are masked, and where the hydroxyl groups at the C-3 positions of both mers are masked with a removable masking group which deactivates the bottom mer;
(c) deprotecting the dimer of step (b) to form a deprotected, masked dimer where the phenolic hydroxyl groups of the top mer are unprotected, where the phenolic hydroxyl groups of the bottom mer are masked, and where the hydroxyl groups at the C-3 positions of both mers are masked;
() catalytically coupling the dimer of step (c) with a protected catechin monomer or a protected epicatechin monomer having an acyloxy activating group at the C-4 position to form a (4→8) trimer where the phenolic hydroxyl groups of the top mer are protected, where the phenolic hydroxyl groups of the middle mer are unprotected, where the phenolic hydroxyl groups of the bottom mer are masked, and where the phenolic hydroxyl groups at the C-3 positions of the middle and bottom mers are masked;
(e) masking the trimer of step (d) to form a trimer where the phenolic hydroxyl groups of the top mer are protected, where the phenolic hydroxyl groups of the middle mer and bottom mers are masked, and where the hydroxyl groups at the C-3 positions of all the mers are masked;
(f) deprotecting the trimer of step (e) to form a trimer where the phenolic hydroxyl groups of the top mer are unprotected, where the phenolic hydroxyl groups of the middle and bottom mers are masked, and where the hydroxyl groups at the C-3 positions of all the mers are masked;
() catalytically coupling the trimer of step (f) with a protected catechin monomer or a protected epicatechin monomer having an acyloxy activating group at the C-4 position to form a (4→8) tetramer; and
(h) optionally repeating the masking, deprotecting, and coupling steps to form a higher oligomer where the number of mers are 5 to 18.

In the following illustrative compounds, P is a protecting group, B is a blocking group, and M is a masking group. The following compound is illustrative of a partially protected procyanidin dimer such as that formed in step (a) above.

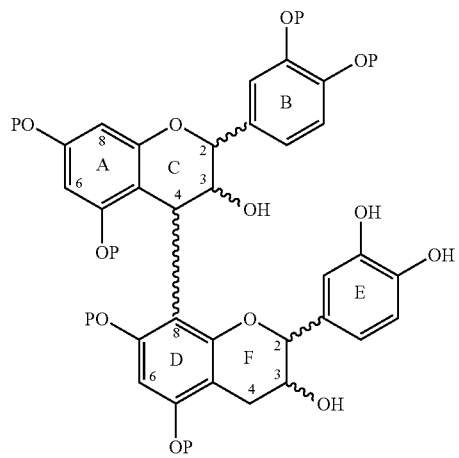

The following compound is illustrative of a protected masked dimer such as that formed in step (b) above.

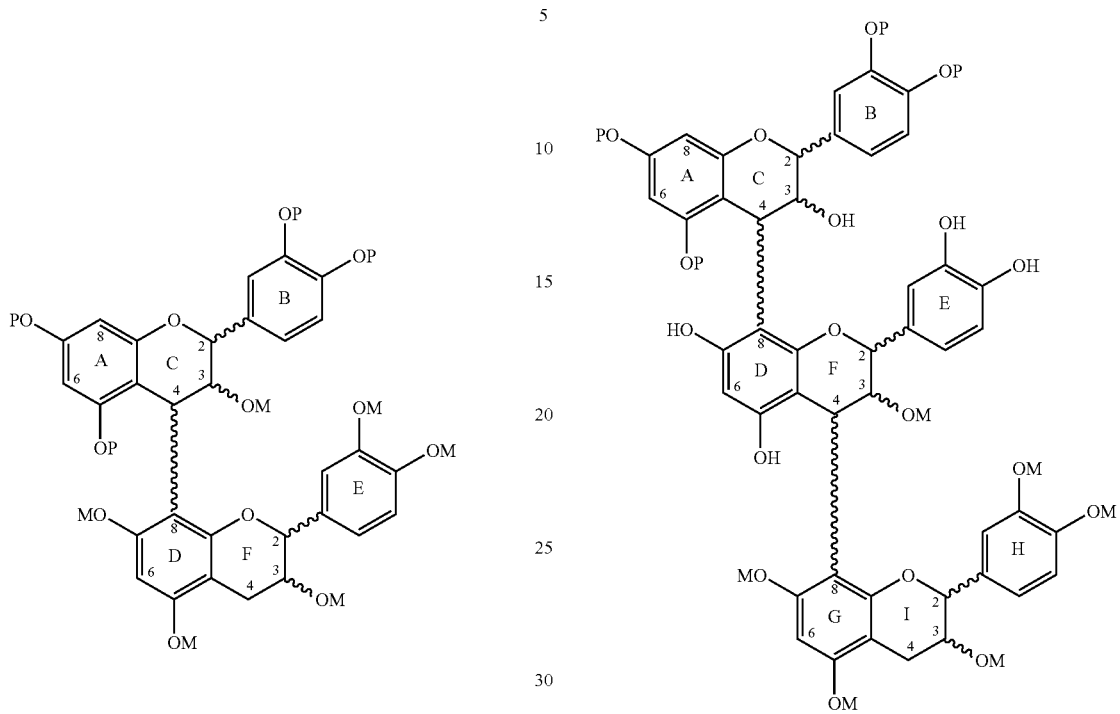

The following compound is illustrative of a deprotected masked dimer such as that formed in step (c) above.

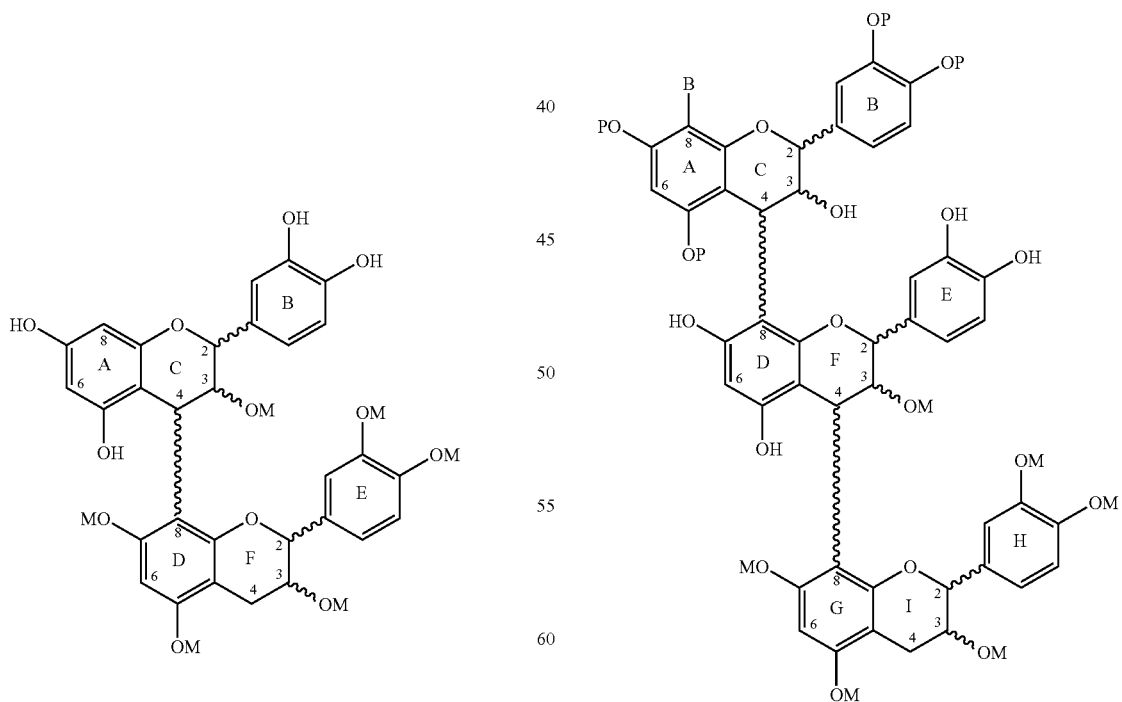

The following compounds are illustrative of a protected, masked, blocked linear trimer and a protected, masked, blocked linear trimer.

The following compounds are illustrative of the unblocked and blocked protected, masked linear trimers of step (d).

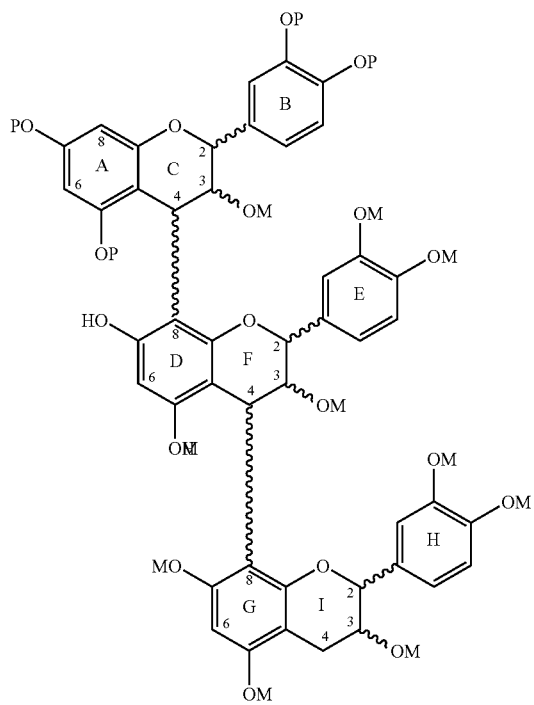
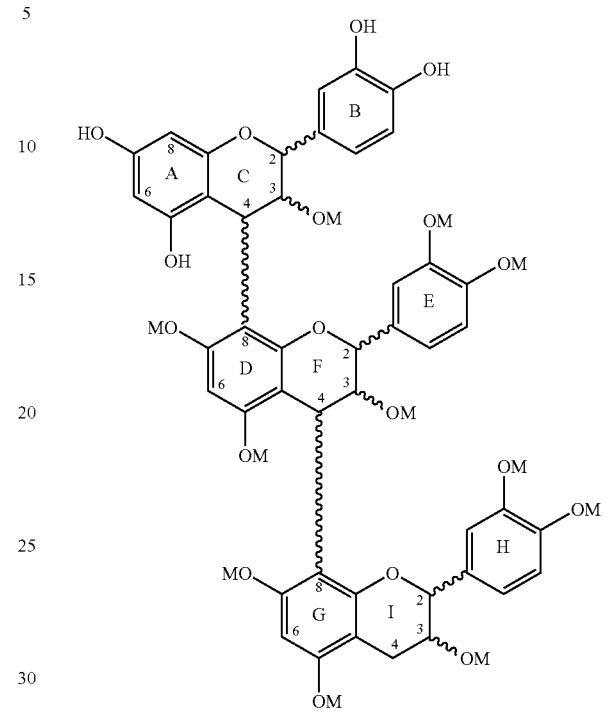
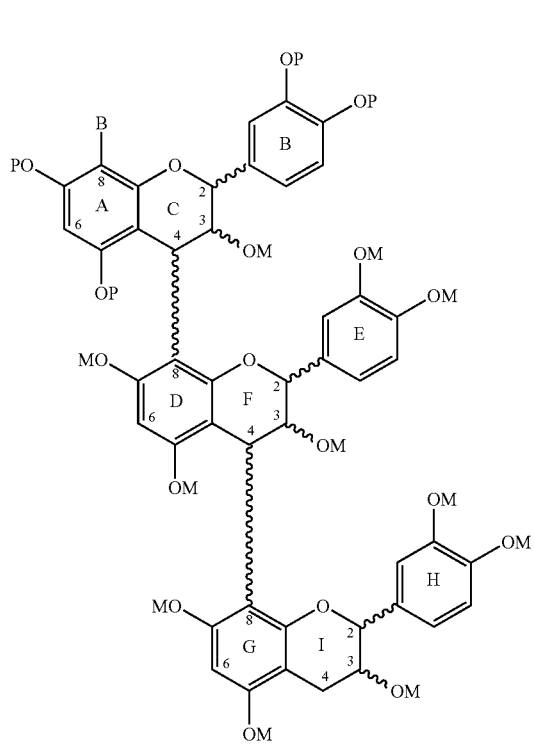
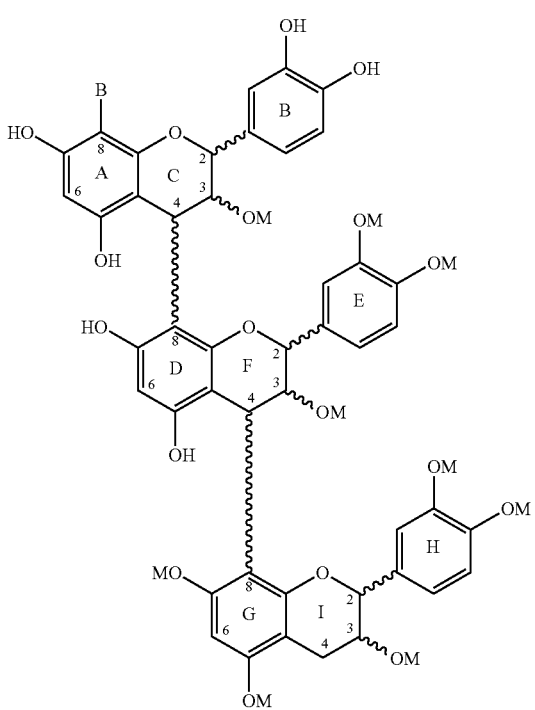
The following compounds are illustrative of the unblocked and/or blocked, deprotected, masked linear trimers of step (e).
The following compounds are illustrative of compounds which result from repeating or alternating steps (a) to (f) to prepare higher oligomers wherein the number of mers is 4.

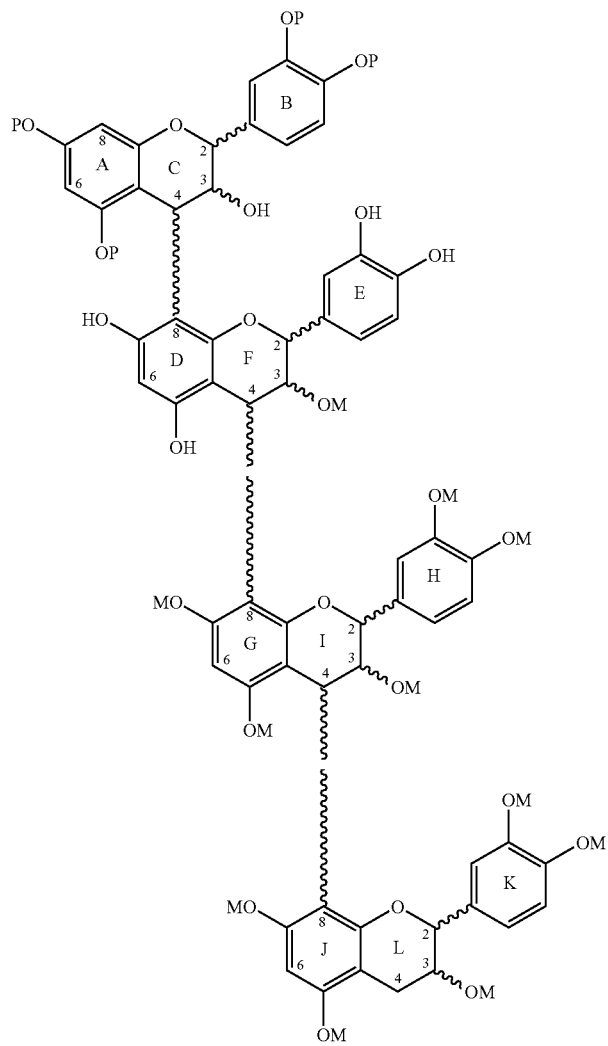
or
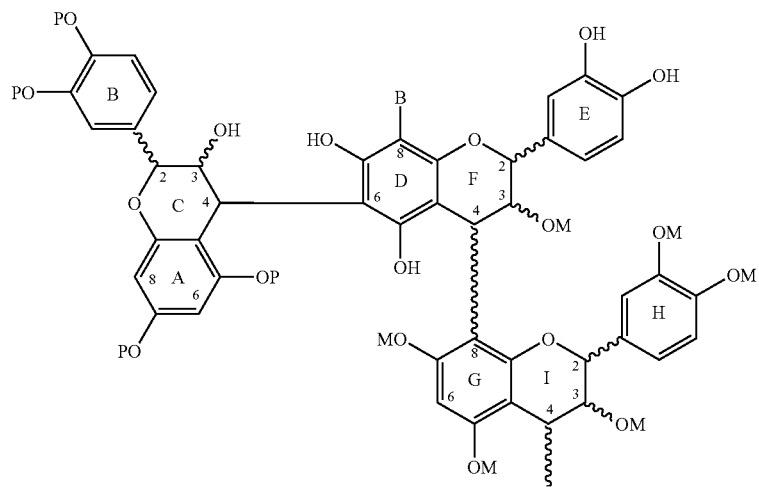

-continued
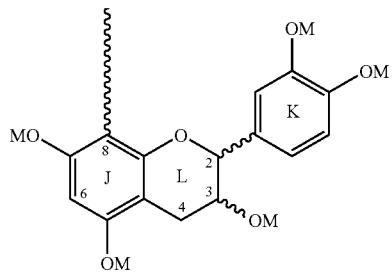
or
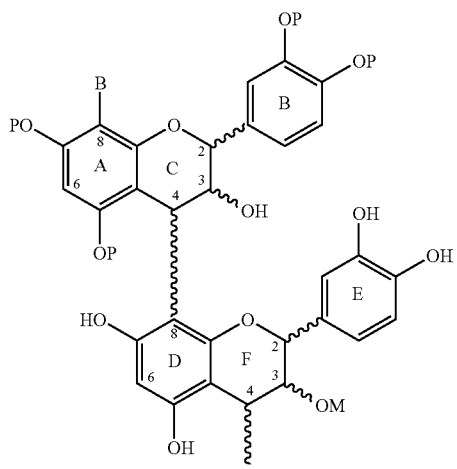
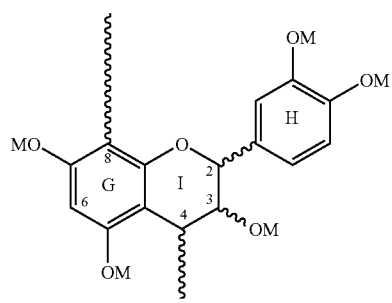
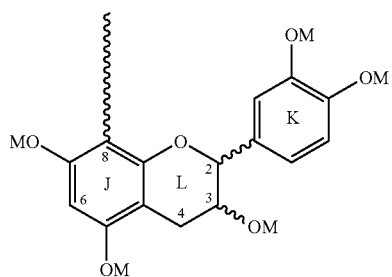
or

-continued

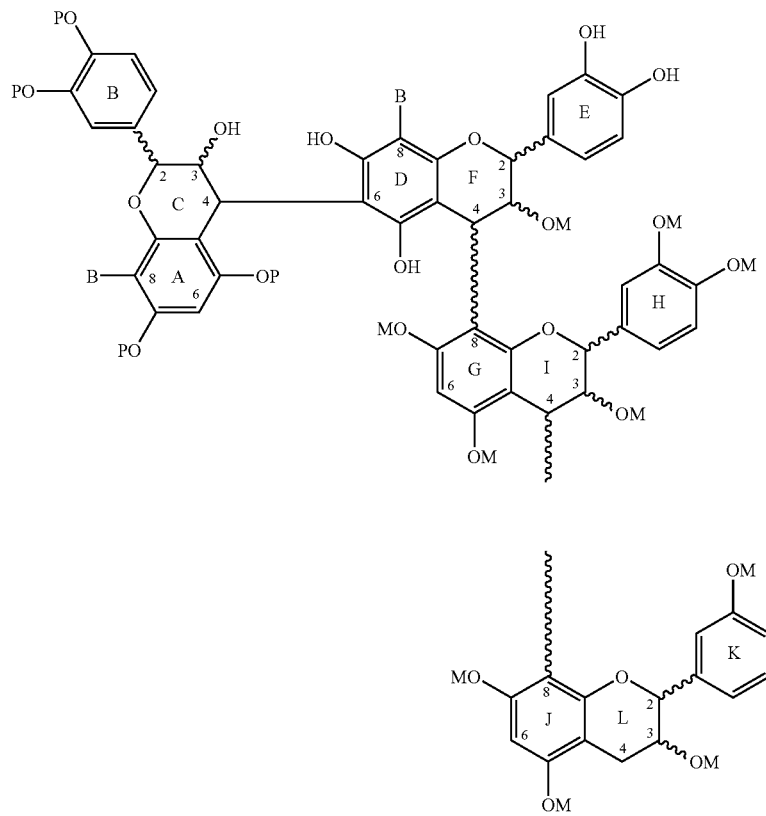

A process is also provided for the preparation of branched procyanidin oligomers. It comprises the steps of:
(a) preparing an unblocked or blocked, partially protected procyanidin dimer, wherein the phenolic hydroxyl groups of the top mer are protected with a removable protecting group which does not deactivate the A ring of the protected mer while the bottom mer has free phenolic hydroxyl groups;
(b) coupling the dimer of step (a) with a unblocked or blocked, protected, activated procyanidin monomer to form a branched trimer;
(c) deprotecting the trimer of step (b); and
(d) optionally carrying out one of the following steps in a sequential, alternating, or combinational fashion to provide procyanidin oligomers having 4 to 18 mers comprising (4→8), (4→6) (6→4), and/or (8→4) linkages;
  i. coupling the oligomer of step (c) with an unblocked or blocked, protected procyanidin monomer;
  ii. masking the oligomer of step (c), deprotecting the masked oligomer, and coupling the masked oligomer with an unprotected or protected, blocked activated procyanidin monomer.

The free phenolic forms of the procyanidin dimers, linear procyanidin oligomers, or branched procyanidin oligomers are obtained by deprotecting the dimers or oligomers and, if necessary, demasking and/or deblocking the dimers or the oligomers. The dimers or oligomers may contain the same or different epicatechin or catechin mers. Preferably n is 5-12, more preferably n is 5. In the linear oligomers the linkages are (4→6) or (6→4) or are (4→8) or (8→4). In the branched oligomers at least one of the linkages is (4→6) or (6→4) and at least one of the linkages is (4→8).

The protecting groups may be benzyl, p-methoxybenzyl, t-butyl, or trityl; benzyl is preferred. An aprotic solvent, e.g., dimethylformamide, dimethylacetamide, or dimethyl sulfoxide, is used in the protecting step; dimethylacetamide is preferred. The acyloxy activating groups are typically acetoxy, formyloxy or propionloxy; acetoxy is preferred. The activation is carried out using a lead (IV) salt, e.g, lead tetraacetate, lead tetraformate, or lead tetraproprionate. Preferably, the activating step is carried out also using an organic acid which is the same as that used in the preparation of the lead salt. Suitable organic acids include formic acid, acetic acid, and propionic acid. The preferred solvent for the activating step is benzene. The blocking group is a halo group, preferably a bromo or an iodo group. The deblocking step is carried out with an alkyl lithium, e.g., tert-butyl lithium or n-butyl lithium. The demasking step is carried out by base hydrolysis. The deprotecting step is carried out by hydrogenolysis.

A doubly branched oligomer having the structure:

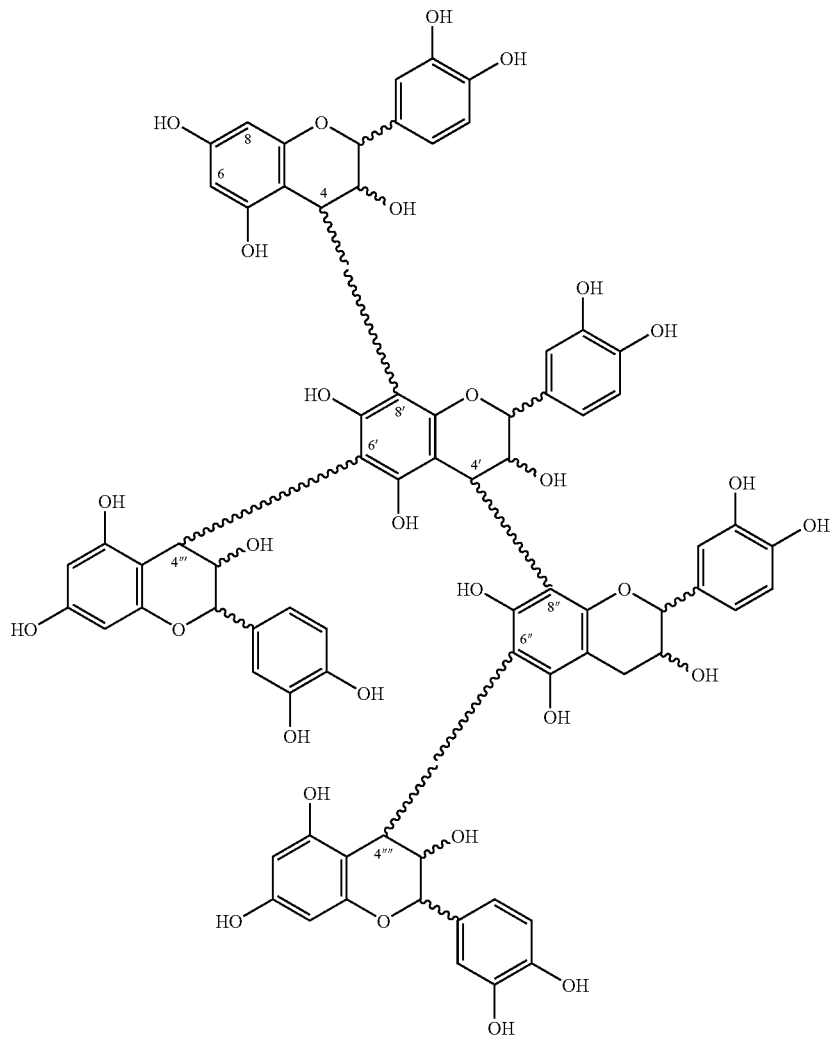

can be prepared by a process which comprises the step of:
(a) protecting each phenolic hydroxyl group of a first procyanidin monomer with a first removable protecting group which does not deactivate the A ring of the monomer, wherein the protecting step is carried out in an aprotic solvent to provide a protected monomer;
(b) activating for coupling the C4 position of the compound of step (a) by introducing an acyloxy group using a lead salt of an organic acid to provide an activated, protected monomer;
(c) coupling the compound of step (b) with an unprotected procyanidin monomer in the presence of a coupling catalyst to provide a partially protected dimer;
(d) masking the dimer of step (c) to provide a masked, partially protected dimer;
(e) deprotecting the masked, partially protected dimer of step (d) to provide a masked dimer;
(f) coupling the masked dimer of step (e) with a 4β-acetoxy protected procyanidin monomer to produce a trimer;
(g) coupling the trimer of step (f) with a 4β-acetoxy procyanidin monomer to produce a procyanidin tetramer;
(h) demasking the tetramer of step (g); and
(i) coupling the tetramer of step (h) with a 4β-acetoxy procyanidin monomer to produce a procyanidin pentamer.

Steps to (i) can be repeated to produce a multiply branched procyanidin oligomer comprising n mers, where n is an integer from 6 to 18.

A process for producing a procyanidin dimer having a (8↔8) linkage is provided. It comprises the steps of:
(a) reacting a first 8-bromo protected monomer with a hexaalkyl distannane in the presence of palladium$_{(o)}$ to provide a protected monomer-8-trialkyl stannane;
(b) coupling the compound of step (a) with a second 8-bromo protected monomer with tetrakis (triphenyl phosphine) palladium$_{(o)}$ in benzene to produce a (8↔8) coupled dimer; and
(c) deprotecting the compound of step (b) to produce the (8↔8) dimer.

A process is also provided for producing a procyanidin dimer having a (6↔6) linkage. The process comprises the steps:

(a) reacting a first 6-bromo protected monomer with a hexaalkyl distannane in the presence of palladium$_{(o)}$ tin to provide a protected monomer-6-trialkyl stannane;

(b) coupling the compound of step (a) with a second 6-bromo protected monomer with tetrakis (triphenyl phosphine) palladium$_{(o)}$ in benzene to produce a (6↔6) coupled dimer; and (c) deprotecting the compound of step (b) to produce the (6↔6) dimer.

A process is also provided for producing a procyanidin dimer having a (6⟷8) linkage. The process comprises the steps of:

(a) reacting a first 6-bromo protected monomer with hexaalkyl distannane in the presence of palladium$_{(o)}$ to provide a protected monomer-6-trialkyl stannane;

(b) coupling the compound of step (a) with a second 8-bromo protected monomer with tetrakis (triphenyl phosphine) palladium$_{(o)}$ in benzene to produce a (6⟷8) coupled dimer; and (c) deprotecting the compound of step (b) to produce the (6⟷8) dimer.

A process is also provided for producing a procyanidin dimer having a (8⟷6) linkage. The process comprises the steps:

(a) reacting a first 8-bromo protected monomer with a hexaalkyl distannane in the presence of palladium$_{(o)}$ to provide a protected monomer-8-trialkyl stannane;

(b) coupling the compound of step (a) with a second 6-bromo protected monomer with tetrakis (triphenyl phosphine) palladium$_{(o)}$ in benzene to produce a (8⟷6) coupled dimer; and (c) deprotecting the compound of step (b) to produce the (8⟷6) dimer.

The present processes offer important advantages and efficiencies over earlier processes for preparing procyanidin oligomers, these include better yields, better selectivity, and easier product isolation. By carrying out the protecting step in dimethylacetamide instead of dimethyl formamide, the partial and full protection of the phenolic hydroxyl groups is more readily controlled.

The present invention further provides crystalline 8-bromo-tetra-O-benzyl (−)-epicatechin when dimethylacetamide is used as the solvent in the protecting step.

DETAILED DESCRIPTION OF THE INVENTION

Monomers comprising procyanidins have the structure:

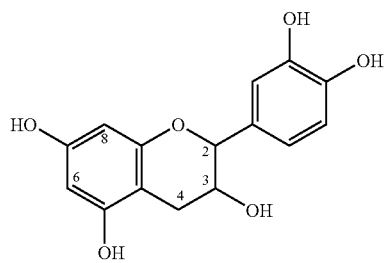

Procyanidins include those found in cocoa beans obtained from *Theobroma cacao* and various related cocoa species, as well as the genus *Herrania* and their inter- and intra-genetic crosses.

Monomers comprising procyanidins include (+)-catechin, (−)-epicatechin and their respective epimers (e.g. (−)-catechin and (+)-epicatechin).

Synthetic linear and/or branched oligomers having the following structures are illustrative of those that can be prepared by the above process.

In the following linear oligomers n is an integer from 0 to 16.

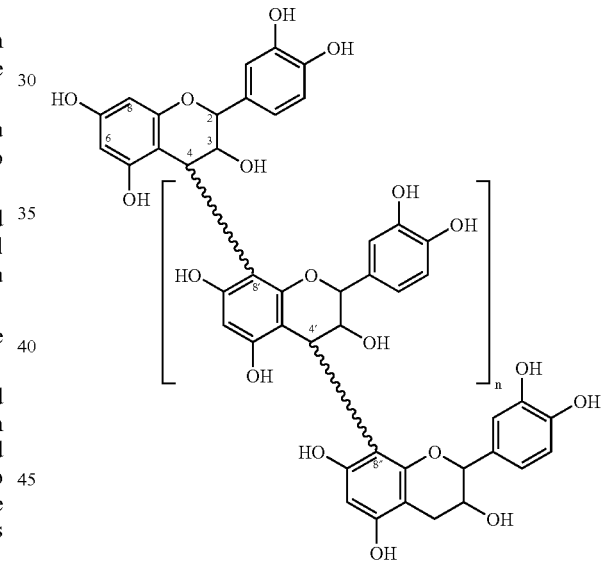

In the following branched oligomers, the mers A and B can be from 1 to 15, with the total number of mers in the final oligomer being from 3 to 18.

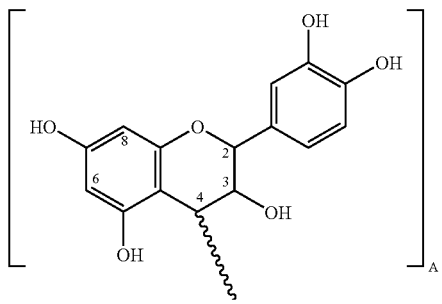

-continued

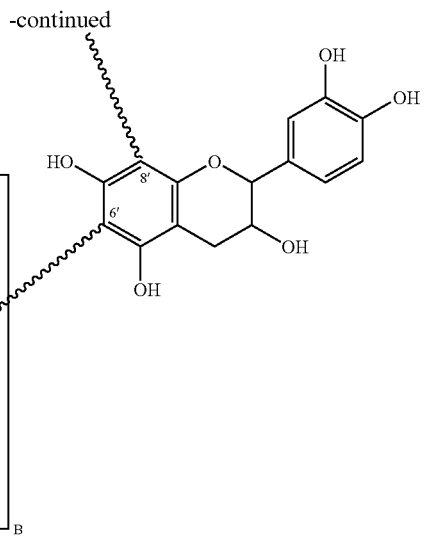

In the oligomers n is an integer from 2 through 18, preferably 3 through 12, more preferably 5 through 12, and most preferably 5. The oligomers have interflavan linkages of (4→6) and and/or (4→8). The oligomers prepared by the inventive process may be represented by the structures above. For the linear oligomer, when x is 0, the oligomer is termed a "dimer"; when x is 1 the oligomer is termed a "trimer"; when x is 2, the oligomer is termed a "tetremer"; when x is 3, the oligomer is termed a "pentamer"; and similar recitations may be designated for oligomers having x up to and including 16 and higher, such that when x is 16, the oligomer is termed an "octadecamer." For the branched oligomer, when B A or B is 1, the oligomer is termed a "trimer"; with similar recitations such as those described for the linear oligomers.

Stereoisomers of the oligomers are encompassed within the scope of the invention. The stereochemistry of the monomers comprising an oligomer can be described in terms of their relative stereochemistry, i.e., "alpha/beta" or "cis/trans", or in terms of their absolute stereochemistry, i.e., "R/S". The term "alpha" (α) indicates the substituent is oriented below the plane of the flavan ring, whereas the term "beta" (β) indicates that the substituent is oriented above the plane of the ring. The term "cis" indicates two substituents are oriented on the same face of the ring, whereas the term "trans" indicates two substituents are oriented on opposite faces of the ring. The terms "R" and "S" are used to denote the arrangement of the substituents about a stereogenic center, based on the ranking of the groups according to the atomic number of the atoms directly attached to the stereogenic center (CIP convention).

There are multiple stereochemical linkages between position C-4 of a flavan 3-ol monomer and positions C-6 and C-8 of the adjacent monomer. The stereochemical linkages between monomeric units is designated herein as (4α→6) or (4β→6) or (4α→8) or (4β→8) for linear oligomers. For linkages to a branched or junction monomer, the stereochemical linkages are (6→4α) or (6→4β) or (8→4β) or (8→4β). When (+)-catechin, designated herein as C, is linked to another C or to (-)-epicatechin, designated herein as EC, the linkages are advantageously (4α→6) or (4α→8). When EC is linked to C or another EC, the linkages are advantageously (4β→6) or (4β→8).

Linear and branched oligomers can be prepared by the methods of the present invention using the steps of protecting, activating, coupling, masking, blocking, deprotecting, demasking and deblocking. In each reaction sequence the catechin or epicatechin monomers can be used to prepare linear or branched oligomers containing the same or different monomers. Higher oligomers can be prepared by repeating the coupling of a dimer, trimer, etc. with an additional catechin or epicatechin monomer using the above steps.

Examples of the compounds which can be synthesized according to the method of the invention include dimers; EC-(4β→8)-EC and EC-(4β→6)-EC, wherein EC-(4β→8)-EC is preferred; trimers [EC-(4β→8)]$_2$-EC, [EC-(4β→8)]$_2$-C, and [EC-(4β→6)]$_2$-EC, wherein [EC-(4β→8)]$_2$-EC is preferred; tetramers [EC-(4β→8)]$_3$-EC, [EC-(4β→8)]$_3$-C, and [EC-(4β→8)]$_2$-EC-(4β→6)-C wherein [EC-(4β→8)]$_3$-EC is preferred; and pentamers [EC-(4β→8)]$_4$-EC, [EC-(4β→8)]$_3$-EC-(4β→6)-EC, [EC-(4β→8)]$_3$-EC-(4β→8)-C, and [EC-(4β→8)]$_3$-EC-(4β→6)-C, wherein [EC-(4β→8)]$_4$-EC is preferred. An example of a branched trimer is

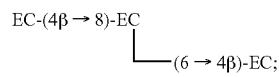

an example of a branched tetramer is

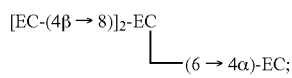

an example of a branched pentamer is

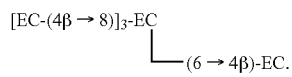

Additional compounds which can be synthesized include the following:

(i) a hexamer, wherein one monomer (C or EC) is linked to a pentamer compound listed above, e.g., [EC-(4β→8)]$_5$-EC, [EC-(4β→8)]$_4$-EC-(4β→6)-EC, [EC-(4β→8)]$_4$-EC-(4β→6)-C, and [EC-(4β→8)]$_4$-EC-(4β→6)-C; wherein [EC-(4β→8)]$_5$-EC- is preferred, with an example of a branched hexamer being

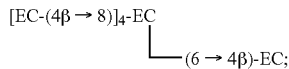

(ii) a heptamer, wherein any combination of two monomers (C and/or EC) is linked to one of the above pentamers, e.g., [EC-(4β→8)]$_6$-EC, [EC-(4β→8)]$_5$-EC-(4β→6)-EC, [EC-(4β→8)]$_5$-EC-(4β→8)-C, and [EC-(4β→8)]$_5$-EC-(4β→6)-C, wherein [EC-(4β→8)]$_6$-EC is preferred with an example of a branched heptamer being

(iii) an octamer, wherein any combination of three monomers (C and/or EC) is linked to one of the above pentamers, e.g., [EC-(4β→8)]$_7$-EC, [EC-(4β→8)]$_6$-EC-(4β→6)-EC, [EC-(4β→8)]$_6$-EC-(4β→6)-C, wherein [EC-(4β→8)]$_7$-EC is preferred with an example of a branched octamer being

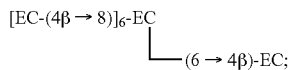

(iv) a nonamer, wherein any combination of four monomers (C and/or EC) is linked to one of the above pentamers, e.g., [EC-(4β→8)]$_8$-EC, [EC-(4β→8)]$_7$-EC-(4β→6)-EC, [EC-(4β→8)]$_7$-EC-(4β→8)-C,[EC-(4β→8)]$_7$-EC-(4β→6)-C, wherein [EC-(4β→8)]$_8$-EC is preferred with an example of a branched nonamer being

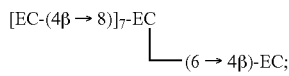

(v) a decamer, wherein any combination of five monomers (C and/or EC) is linked to one of the above pentamers, e.g., [EC-(4β→8)]$_9$-EC, [EC-(4β→8)]$_8$-EC-(4β→6)-EC, [EC-(4β→8)]$_8$-EC-(4β→8)-C, [EC-(4β→8)]$_8$-EC-(4β→6)-C, wherein [EC-(4β→8)]$_9$-EC is preferred with an example of a branched decamer being

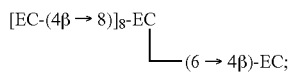

(vi) an undecamer, wherein any combination of six monomers (C and/or EC) is linked to one of the above pentamers, e.g., [EC-(4β→8)]$_{10}$-EC, [EC-(4β→8)]$_9$-EC-(4β→6)-EC, [EC-(4β→8)]$_9$-EC-(4β→8)-C, [EC-(4β→8)]$_9$-EC-(4β→6)-C, wherein [EC-(4β→8)]$_{10}$-EC is preferred with an example of a branched undecamer being

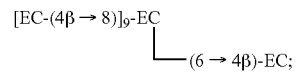

(vii) a dodecamer, wherein any combination of seven monomers (C and/or EC) is linked to one of the above pentamers, e.g., [EC-(4β→8)]$_{11}$-EC, [EC-(4β→8)]$_{10}$-EC-(4β→6)-EC, [EC-(4β→8)]$_{10}$-EC-(4β→8)-C, [EC-(4β→8)]$_{10}$-EC-(4β→6)-C, wherein [EC-(4β→8)]$_{11}$-EC is preferred with an example of a branched dodecamer being

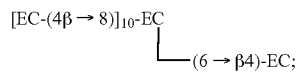

The aforementioned list of oligomers is illustrative and is provided to illustrate the types of compounds that can be prepared by the methods of the invention and is not an exhaustive list of compounds encompassed by the invention. The oligomers can be separated and purified by the methods disclosed in U.S. Pat. No. 5,554,645 issued Sep. 10, 1976 to Romanczyk et al. and U.S. Pat. No. 5,712,305 issued Jan. 27, 1998 to Romanczyk et al.

One skilled in the art will appreciate the rotation of a number of bonds within an oligomer can be restricted due to steric hindrance, particularly if the oligomer is substituted, such as with benzyl groups. Accordingly, all possible regioisomers and stereoisomers of the compounds prepared by the invention are encompassed within the scope of the invention.

Definitions

As used herein, a "protecting group" is a removable group which replaces the hydrogen of the phenolic hydroxyl groups in the procyanidin monomers or oligomers. The group should be removable under conditions which do not affect the procyanidin oligomers.

As used herein, a "blocking group" is a removable group which directs the coupling by blocking the C-8-position of the A ring of a catechin or epicatechin monomer or a procyanidin oligomer, thus directing coupling with another procyanidin monomer to occur at the C-6 position of the A ring. The group should be removable under conditions that do not affect the procyanidin oligomer.

As used herein, a "masking group" is a removable group which masks the unprotected phenolic hydroxyl and the C-3 hydroxyl group(s) of a procyanidin monomer or higher oligomer during the coupling of the dimer or higher oligomer with another procyanidin monomer. The group should be removable under conditions that do not affect the procyanidin oligomer.

As used herein, an "activating group" is an acyloxy group which activates the C-4position of the C ring of a procyanidin monomer, dimer, or higher oligomer and results in coupling with another procyanidin monomer or oligomer at that position.

The term "combinational" used herein refers to the possible regiochemical linkage possibilities for preparing any given procyanidin oligomer. For instance, a linear procyanidin tetramer can be comprised of (4→8) and (4→6) linkages between the monomers comprising the tetramer. For synthesis purposes these linkages result in separate compounds which can have different biological activity. For structure-activity studies it would be advantageous to provide a series of these oligomers to determine the importance of regiochemical linkages to biological activity. For a linear tetramer the possible linkages are as follows:

| Tetramer 1 | Tetramer 2 | Tetramer 3 | Tetramer 4 | Tetramer 5 | Tetramer 6 | Tetramer 7 | Tetramer 8 |
|---|---|---|---|---|---|---|---|
| 4 → 8 | 4 → 6 | 4 → 8 | 4 → 8 | 4 → 6 | 4 → 6 | 4 → 6 | 4 → 8 |
| 4 → 8 | 4 → 6 | 4 → 8 | 4 → 6 | 4 → 8 | 4 → 6 | 4 → 8 | 4 → 6 |
| 4 → 8 | 4 → 6 | 4 → 6 | 4 → 8 | 4 → 8 | 4 → 8 | 4 → 6 | 4 → 6 | which necessitate the need for a synthetic procedure to prepare 8 different tetramers, each requiring different steps for preparation.

Protecting Groups

The protecting groups useful in this invention are electron donating moieties that function to activate catechin and epicatechin monomers at the C-4 position. In the C-4 activation reaction, electron donating phenolic protecting groups function to stabilize, and thereby assist in the formation of the intermediate C-4 benzylic cation formed by oxidation of the protected monomer with a lead (IV) salt. In the coupling reaction, an electrophilic aromatic substitution reaction, the electron donating phenolic protecting groups function again to stabilize, and thereby assist in the formation of the C-4 benzylic cation by treatment of the C-4 acyloxy substituted catechin or epicatechin monomer (an activated monomer) with a Lewis acid catalyst. In the coupling reaction, the electron donating phenolic protecting groups also function to increase the differences in reactivity between the various aryl moieties that may be present in the reaction. As described below, unprotected catechin or epicatechin monomers or selected unprotected (deprotected) monomeric units of a procyanidin oligomer are used as nucleophiles in the coupling reaction. The C-4acyloxy substituted, protected catechin or epicatechin monomer, on treatment with a Lewis acid, functions as the electrophile. The unprotected procyanidins function as nucleophiles because they process higher election densities, that is higher nucleophilicities, than the protected procyanidin monomers. Any self-coupling between protected procyanidin monomers is limited due to the comparatively higher nucleophilicities of the unprotected procyanidins.

Among the various protecting groups, benzyl groups are preferred because they are more easily removed under mild conditions such as hydrogenolysis. Another advantage of benzylation (except, for example, p-nitro benzylation) is that it will not deactivate the aromatic ring toward coupling when the procyanidin monomers or oligomers are acting as nucleophiles. Surprisingly and quite unexpectedly, changing the aprotic organic solvent used in the protecting step from dimethyl formamide (DMF) to dimethyl acetamide (DMA) resulted in an increased yield of the protected oligomer, perhaps due to the fact that the slightly higher dielectric constant of DMA may be favoring the O-alkylation. The yield was at least about 50%, typically about 60% to about 70%. In addition, no extra clean-up procedures were required and the products were readily crystallized. Examples 1 and 2 describe the specific conditions for the preparation of tetra-O-benzyl-(+)-catechin and tetra-O-benzyl-(−)-epicatechin. Further investigation of the solvent system indicated that potassium carbonate ($K_2CO_3$) was preferred over sodium carbonate ($Na_2CO_3$) because of its solubility within the preferred solvent system. It was found that potassium iodide can be used in catalytic amounts in combination with benzyl bromide.

Another useful protecting group for (−)-epicatechin is p-methoxy benzyl (PMB) groups. If PMB is selected as a protecting group in preparing a partially protected procyanidin dimer, then the protecting step further comprises acetylating the procyanidin monomer followed by treatment with sodium hydride, PMB-chloride and DMF in water to remove the phenolic acetate groups, resulting in alkylation of the phenoxide ions with PMB. When utilizing DMA as the solvent in the protecting step, PMB groups should not be used. Tetra-O-PMB-(−) epicatechin can be prepared using the procedure by Kawamoto, H., Nakatsubo, F. and Murakami, K. *Synth. Commun.*, 26, 531-534 (1996). Pentaacetyl(−)-epicatechin is first prepared (as described in Example 3 below) by treatment with sodium hydride (NaH), p-methoxybenzyl chloride (PMBC1), dimethyl formamide (DMF) and water in an amount sufficient (4 eq) to generate the equivalent amount of base to remove the four phenolic acetate groups in succession. The resultant phenoxide ions undergo rapid alkylation with the PMBC1. Examples 4 and 5 describe the specific conditions by which penataacetyl (+)-catechin and tetra-O-p-methoxybenzyl-3-acetyl-(−) epicatechin were prepared.

The skilled artisan will recognize that other protecting groups such as tert-butyl, trityl and 2,4-dimethoxy benzyl can be used C-4 Activation Altering the LTA reaction conditions to 1:1 benzene:acetic acid eventually produced the highest yield (60-70%) and the stereospecific 4β product. Other useful solvent mixtures include benzene, toluene, chlorobenzene, cyclohexane, heptane, carbon tetrachloride, or mixtures thereof, admixed with an organic acid, which is the same as that used to prepare the lead (IV) salt used in the activation reaction.

The lead salts of organic acids are employed in the activation step, e.g., lead tetraformate, lead tetrapropionate, and the like. Preferably, the corresponding organic acids, i.e., formic and propionic acids, are used in combination with the lead salt to improve the yield. The preferred salt is lead acetate and the preferred combination is lead tetraacetate and acetic acid.

Examples 6-9 describe the specific conditions for the preparation of 4β-acetoxy tetra-O-benzyl-(−) -epicatechin, 4β-hydroxyl tetra-O-benzyl-(+)-catechin, 4βhydroxyl tetra-O-benzyl-(−)-epicatechin, and 4β-acetoxy tetra-O-benzyl-(+)-catechin.

Masking Groups

The masking groups useful in this invention are electron withdrawing moieties that function to deactivate selected monomeric units of procyanidin oligomers in the electorphilic aromatic substitution coupling reaction described hereinbelow. When procyanidin oligomers are used in the coupling reaction, it is imperative that an activated monomer does not randomly react with different monomeric units of the oligomer. Masking groups are used to increase the differences in reactivity between the different monomeric units of an oligomer. Use of electron withdrawing moieties as masking groups deactivates the monomeric units of the oligomer bearing the masking groups towards coupling with an activated, protected monomer. Accordingly, in the process of this invention, an activated monomer selectively reacts with an unprotected monomeric unit of a partially masked oligomer due to the high reactivity (nucleophilicity) of the unprotected monomeric unit and the reduced reactivity of the masked monomeric units of the oligomer.

Masking groups that are useful in the process of this invention include acyl groups such as acetyl and propionyl, aroyl groups such as benzoyl, carbamate groups such as N-phenyl carbamate, carbonate groups such as methyl carbonate, and arylsulfonyl groups such as 2,4-dinitrobenzenesulfonyl. Preferably, the masking group is acetyl. Masking of unprotected phenolic hydroxyl and C-3 hydroxyl groups of procyanidin oligomers may be accomplished using any conventional technique for replacing the hydrogen of the hydroxyls with suitable masking groups such as those identified above. The reagents used will depend on the masking groups being introduced and are well known in the art.

Coupling Reaction

In the process of this invention, the use of a coupling catalyst such as a Lewis acid (e.g. lithium bromide) is preferred. The use of a 4β-acetoxy derivative as the electrophile is also preferred. The selectivity of the coupling reaction is significantly improved thereby. The use of the Li$^+$ as a counter ion favored C-alkylation over O-alkylation.

When methanol is added to a refluxing methylene chloride solution of 4βacetoxytetra-O-benzyl-(+)-catechin and LiBr, 4β-methoxy tetra-O-benzyl-(+)-catechin is formed in significantly higher yield (see Example 10). The β stereochemistry is assigned on the basis of the coupling constant of 3.5 Hz between H-3 and H-4 which indicates a cis relationship. This reaction does not occur when a halide such as LiBr is not employed as the Lewis acid. In this reaction, the acetoxy is displaced by the halide which then immediately reacts with the methanol, acting as a nucleophile, thereby driving the reaction to equilibrium.

It was unexpected that the use of LiBr as the Lewis acid would drive the coupling reaction between 4β-acetoxy tetra-O-benzyl monomer and another monomer acting as the nucleophile, thereby eliminating the step of preparing a 3,4 diol of the monomer.

To test this unexpected finding and gain insight into the potential application of this reaction, 4β-acetoxy tetra-O-benzyl-(+)-catechin was reacted with (−)-epicatechin in the presence of LiBr as described in Example 11. The resultant dimer obtained was 90% pure and the yield was 62%. The $^1$H NMR spectrum indicated one singlet at δ 5.85 for 1H and a pair of doublets at δ 6.19 and 6.16 each integrating to 1H with a typical m-coupling of 1.5 Hz which indicated the formation of only one isomer. Treatment of the dimer with acetic anhydride/pyridine formed the hexaacetate (Example 13) and, as expected, the singlet for the C-6' hydrogen shifted downfield to δ 6.52. The doublet for the C-4 hydrogen had a coupling constant of 9.6 Hz, indicating the a configuration. The partially benzylated dimer was deprotected with hydrogen/palladium$_{(o)}$ (H$_2$/Pd) to obtain the dimer (+)-catechin-(4α→8)-(−)-epicatechin (see Example 12). HPLC analysis indicated that, in addition to the above dimer, another unknown dimer (13.5%) was present as well as a trace amount of trimer and tetramer. Final confirmation of the dimer's structure was made by preparing the octaacetate and comparing the $^1$H NMR to the literature (Kawamoto, H., Nakatsubo, F. and Murakami, K., *J. Wood Chem. Tech.*, 9, 35-92 (1989)).

To study the surprising results using the LiBr coupling reaction, the coupling between 4β-acetoxy tetra-O-benzyl-(−)-epicatechin and (−)-epicatechin was performed as described in Example 15 (refer to Example 17 for the catechin dimer). The dimer (−)-epicatechin-(4β→8)-(−)-epicatechin was obtained after hydrogenolysis (Example 16). As shown in the following table, appreciable amounts of trimers and tetramers occurred in this reaction.

TABLE 1

| | LiBr Coupling Reaction | | | |
|---|---|---|---|---|
| Monomer 1 | Monomer 2 | % Dimer* | % Trimer* | % Tetramer* |
| 4β-acetoxy tetra-O-benzyl (+)-catechin | (−)-epicatechin | 71.4, 13.5 | 3.8 | 4.7 |
| 4β-acetoxy tetra-O-benzyl (−)-epicatechin | (−)-epicatechin | 44.7 | 16.8, 9.3 | 4.5, 3.3 |
| 4β-acetoxy tetra-O-benzyl (+)-catechin | (+)-catechin | 68.0** | — | — |

*HPLC-MS analysis in negative ion mode (NH$_4$OH) @ 0.04 mL/min; fragmentor 75; Vcap 3000. (See also FIGS. 1A and 1B).
**Yield based on silica gel chromatography.

This table indicates that only one primary dimer results from this reaction. The manipulation of reaction time and amounts of reactant monomers can reduce the presence of higher oligomers. Additionally, it has been observed that tetra benzyl-monomers do not act as nucleophiles in the lithium bromide coupling reaction. The free phenolic hydroxyl groups are necessary to increase the activity of the aromatic ring towards coupling. This is significant, since it offers a means to differentiate between rings capable of participating in the coupling and rings not capable of participating in the coupling.

Coupling reaction yields have also been improved by using lithium iodide (Li I) as Lewis Acid (see Example 20). Also, the reaction between 4β-acetoxy tetra-O-benzyl-(+)-catechin and (−)-epicatechin was completed in only 18 hours with a yield of 85% after chromatography. In Example 11 where lithium bromide was used, and the yield was only 62% after 24 hours.
This coupling procedure can be used for higher oligomers other than the dimer as shown in the following reaction schemes.
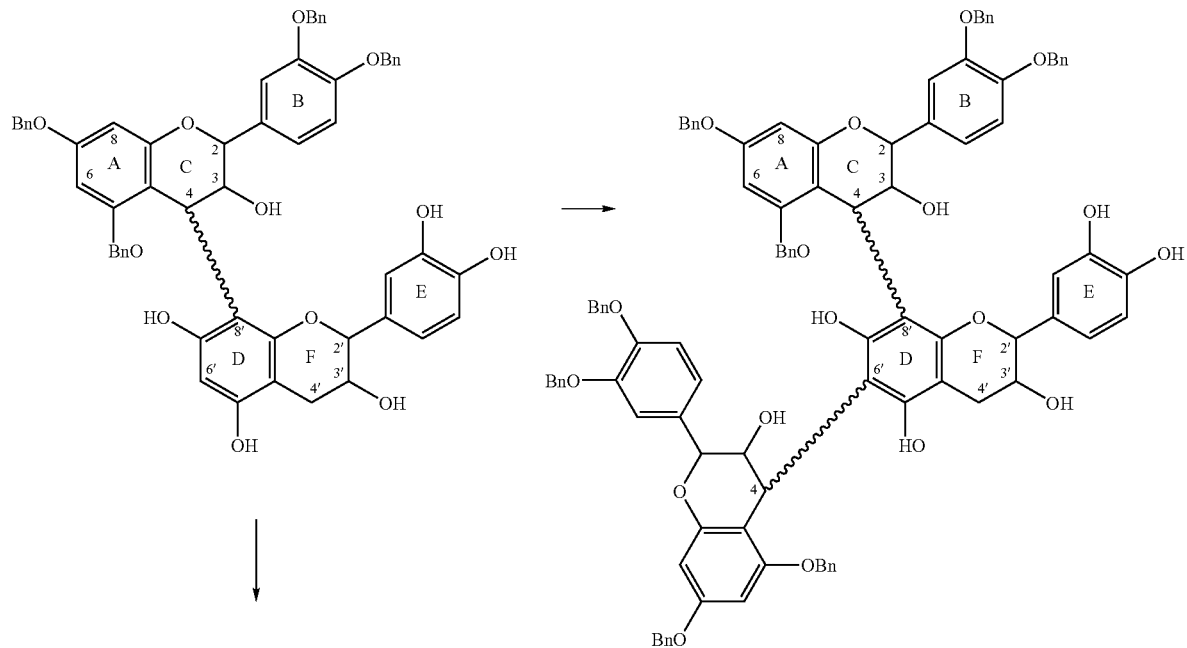
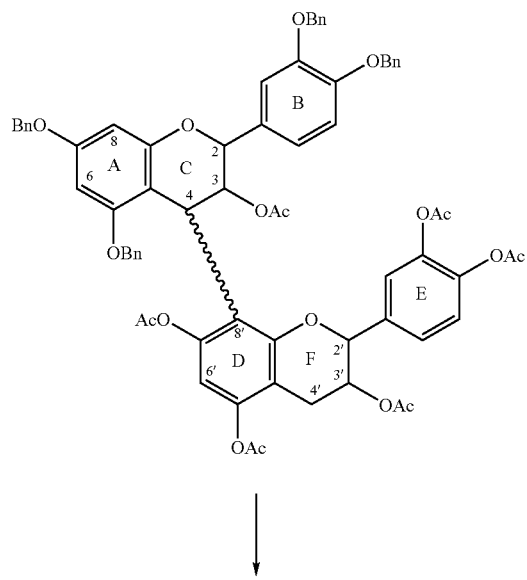

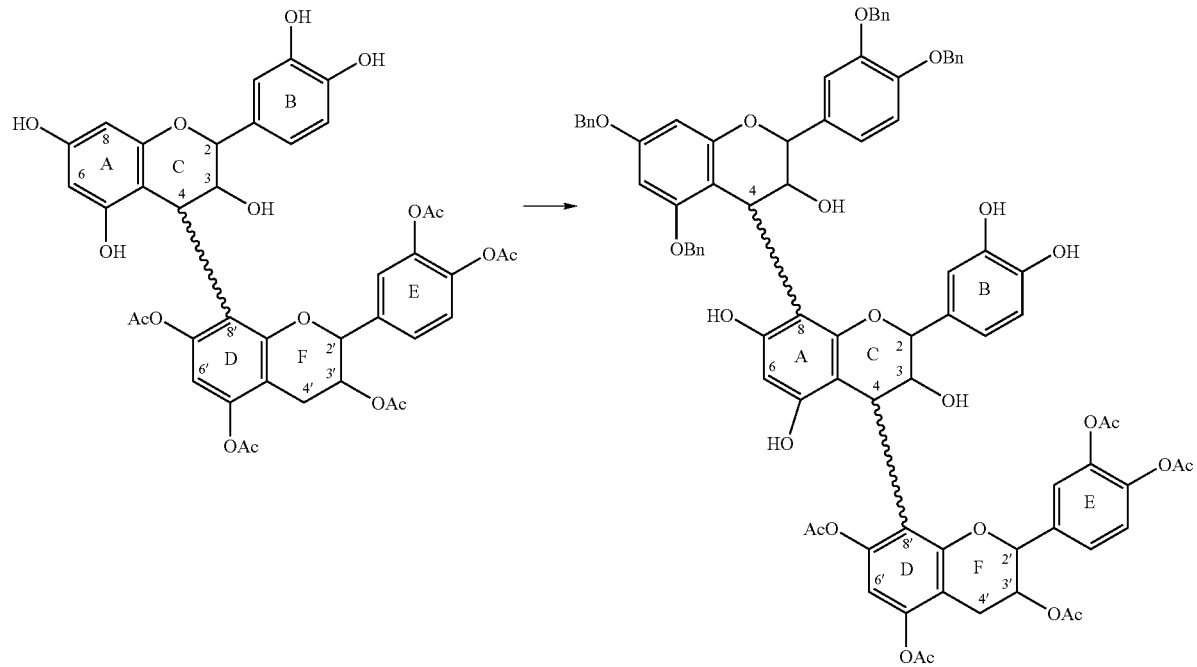

Since the phenolic hydroxyl groups in the A ring are benzylated, coupling occurs only at the C-6' position of the D ring and leads to the formation of a branched trimer. This was successfully tested by reacting tetra-O-benzyl-(+)-catechin-(4β→8)-(−)-epicatechin (see Example 11) with 4β-acetoxy tetra-O-benzyl -(+)-catechin (see Example 6) with LiBr in THF-methylene chloride. A spot was isolated from Thin Layer Chromatography (TLC) where the $^1$H NMR was too complicated to interpret. However, mass spectral analysis showed that the molecular ion peak at m/z 1861 corresponded to the desired structure in which one of the hydroxyl groups was not acetylated. The reaction was repeated and the same product isolated. The mass spectrum clearly showed the formation of this branched trimer where (M+Na)$^+$ at m/z 1610 and (M+H)$^+$ at m/z 1588 were observed with typical retro Diels Alder cleavage fragmentation. A third replicate reaction was conducted for a longer time and again the mass spectrum was consistent with a branched trimer whose tentative structure was assigned as tetra-O-benzyl-(+)-catechin-(4α→8)-(−)-epicatechin-(6→4α)-tetra-O-benzyl-(+)-catechin (see Example 24).

For the synthesis of linear oligomers, a strategy of selective activation-deactivation of the rings capable of participating in the coupling reaction was developed. In this case, the partially benzylated dimer was acetylated and then hydrogenolysed, allowing the preparation of a dimer with free phenolic hydroxyl groups (OH groups) in the A/B rings, and with acetate groups in the D/E rings. The electron withdrawing acetyl groups deactivated the D ring and thus allowed coupling with the 4β-acetoxy monomers to occur regioselectively at the C-8 position of the A ring. The resultant trimer can be subjected to the same process of acetylation and debenzylation followed by coupling with another 4β-acetoxy monomer to produce a tetramer. Repetitions of these steps leads to oligomers of increasing size.

This process was confirmed where the partially protected dimer of Example 11 was acetylated (see Example 13) and then hydrogenolysed (see Example 14). Doubling of NMR peaks was observed which is indicative of rotamers. NMR spectra taken at higher temperatures (313° K) simplified the spectrum, confirming the existence of the rotamers. Interestingly, performing the hydrogenolysis in ethyl acetate enabled the isolation of mono-O-benzyl-3-acetyl-(+)-catechin (4α→8)-pentaacetyl-(−)-epicatechin. When this oligomer was hydrogenolysed, the product was the same as that obtained previously. Reacting 3-acetyl-(+)-catechin-(4α→8)-pentaacetyl-(−) -epicatechin (see Example 14) with 4β-acetoxy tetra-O-benzyl-(−)-catechin (see Example 6) resulted in the desired product, i.e., tetra-O-benzyl (+)-catechin (4α→8)-3-acetyl (+)-catechin (4α→8)-pentaacetyl (−) -epicatechin (see Example 20). The mass spectrum (APCI, negative ion mode) indicated a strong molecular ion peak at m/z 1479.6 which was identical to the calculated mass for $C_{85}H_{74}O_{24}$ (1479.5). Mass fragments at m/z 1437, 1389 and 1347 were consistent for the loss of acetyl, benzyl and acetyl/benzyl groups from the parent compound. FAB MS showed a molecular ion peak at m/z 1482 (M+H)$^+$ and a fragmentation pattern consistent for tetra-O-benzyl-3-acetyl(+)-catechin-(4α→8) -pentaacetyl-(−)-epicatechin.

Similarly, the linear tetramer was formed by preparing tetra-O-benzyl-(+)-catechin-(4α→8)-3-acetyl-(+)-catechin-(4α→8)-pentaacetyl(−)-epicatechin (see Example 20) which was acetylated to tetra-O-benzyl-3-acetyl-(+)-catechin-(4α→8)-pentaacetyl-(+)-catechin-(4α→8)-pentaacetyl (−)-epicatechin (see Example 21). Hydrogenolysis of the above compound (see Example 22) produced 3-acetyl-(+)-catechin-(4α→8)-pentaacetyl-(+)-catechin-(4α→8)-pentaacetyl (−)-epicatechin. Coupling 3-acetyl-(+)-catechin-(4α→8)-pentaacetyl-(+)-catechin-(4α→8)-pentaacetyl (−)-epicatechin with 4βacetoxy tetra-O-benzyl-(+)-catechin (see Example 6) resulted in the formation of the tetramer tetra-O-benzyl-(+)-catechin-(4α→8)-3-acetyl pentaacetyl-(+)-catechin-(4α→8)-pentaacetyl-(+)-catechin-(4α→8)-pentaacetyl (−)-epicatechin (see Example 23). The FAB mass spectrum showed the molecular ion peak at m/z 1978 which is consistent with the structure.

An in situ replacement of the phenolic acetate groups with benzyl groups has also been developed. The in situ replacement of the acetyl for benzyl groups was conducted on 3-acetyl-tetra-O-benzyl-(+)-catechin-(4α→8)-pentaacetyl-(−)-epicatechin (see Example 13) using the conditions specified in Example 18 to result in the preparation of 3-acetyl-tetra-O-benzyl-(+)-catechin-(4α→8)-3-acetyl-tetra-O-benzyl-(−)-epicatechin. Hydrogenolysis (see Example 19) provided the recovery of tetra-O-benzyl-(+)-catechin-(4α→8)-tetra-O-benzyl-(−)-epicatechin which was then hydrogenolysed to the free dimer, proving the feasibility of this procedure.

Blocking Groups

On the basis of the above steps, methods for the synthesis of (4→6) interflavan linkages between monomers have been developed. For example, monomers can be benzylated in high yields using the DMA solvent system previously described. The benzylated monomers can be brominated at the C-8 position to provide 8-bromo-tetra-O-benzyl monomers as shown in Examples 25 and the several variants shown in Examples 26, and 27, and Example 28 describes the absolute stereochemistry for 8-bromo-tetra-O-(−)-epicatechin. Deprotecting these derivatives results in the preparation of the 8-bromo monomers. The resultant bromo derivative effectively blocks coupling at the C-8 position, thus directing coupling to occur at the C-6 position. Coupling of the 8-bromo monomers with 4β-acetoxy tetra-O-benzyl-monomer under the conditions of the lithium bromide procedure results in the formation of a (4→6) dimer. A typical reaction scheme is illustrated below.

Debromination (i.e., deblocking) is effected at low temperature (−78° C.) in solution with a suitable alkyl lithium compound such as n-butyl lithium or tert-butyl lithium, followed by protonation of the resultant dimer by a weak protic acid (e.g., water). By employing the additional steps embodied in the invention, the (4→6) dimer can be extended to higher oligomeric size, comprising variations of regio- and stereochemistry previously described.

Deprotection and Demasking

The reagents used in the deprotection step will depend upon the group being removed. For example, when removing the benzyl protecting groups, hydrogenolysis is carried out using the conditions set forth in Examples 12, 16 and 22. When the masking groups are removed, alkaline hydrolysis is carried out using the conditions set forth in Examples 5 and 18.

Alternatively, commercial lipase can be used to enzymatically deacetylate the protected oligomer. Removal of the protecting or masking groups can be accomplished using any conventional techniques provided the techniques do not adversely affect the procyanidin oligomer.

Compounds of the Invention

Novel compounds that can be produced by the process of the invention include novel multiple branched, preferably doubly branched, procyanidin oligomers represented by the following structure.

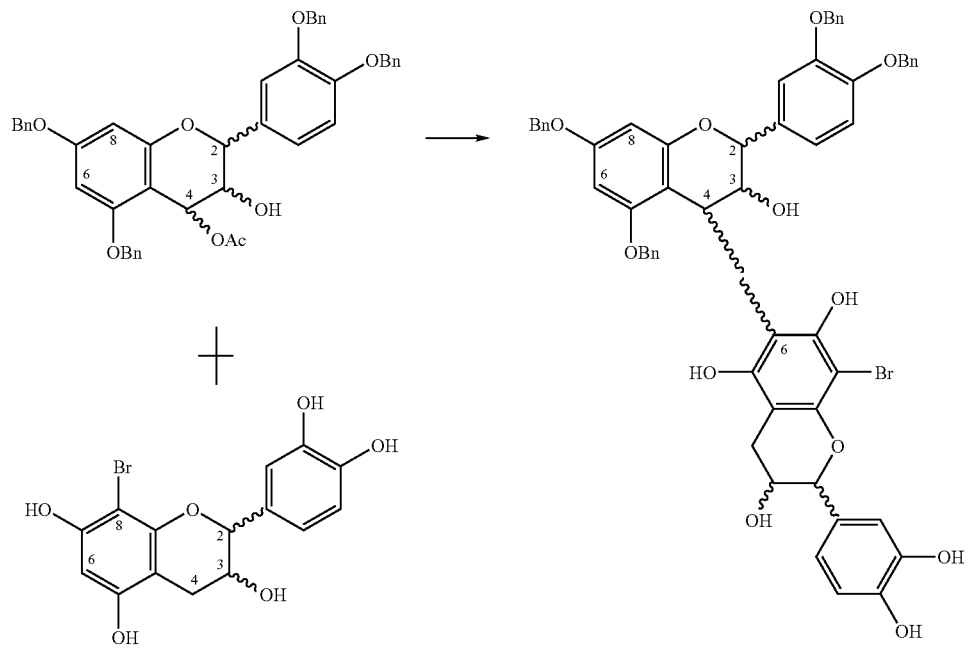

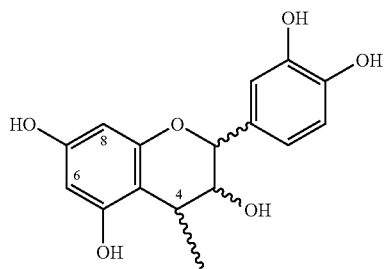
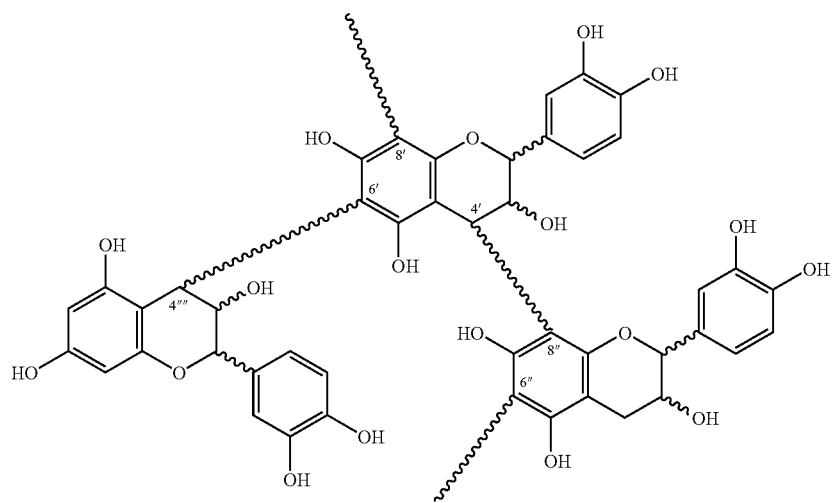
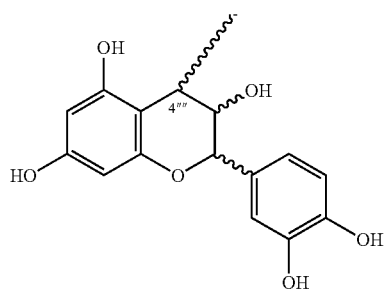

Other compounds that can be produced include procyanidin oligomers comprised of (8↔8), (6↔8), and (6↔6), linkages, where representative structures are shown below.

Procyanidin oligomer with (8↔8) linkage

Procyanidin oligomer with (8↔6) linkage

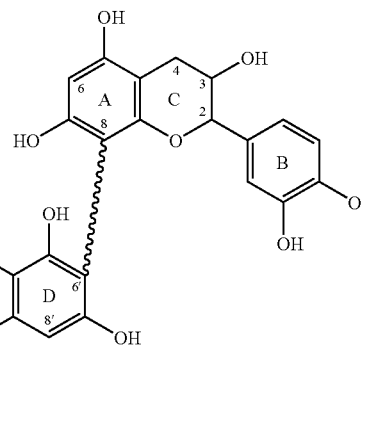

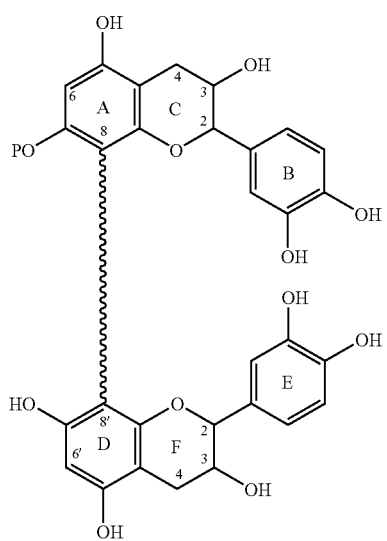

The steps outlined above under the Blocking Groups Section, can be extended to produce procyanidin oligomers comprising (6↔6), (6↔8), (8↔8) interflavan linkages. These compounds can be obtained from 8-bromo- or 6-bromo-monomer intermediates. Coupling of these compounds with arylboronic or arylstannanes obtained from the same halogenated intermediates by Suzuki coupling or by Stille reactions leads to the desired oligomeric linkages (Suzuki, A., *Pure Appl. Chem.* 57, 11749-11758 (1985), Stille, J. K., *Agnew, Chem. Internal. Ed. Engl.*, 25, 508-524 (1986)).

Uses of the Procyanidin Oligomers

The oligomers have the same uses, and can be formulated, purified and administered in the same manner as described in U.S. Pat. No. 5,554,645 issued Sep. 10, 1996 to Romanczyk et al. and U.S. Pat. No. 5,712,305 issued Jan. 27, 1998

Procyanidin oligomer with (6↔6) linkage

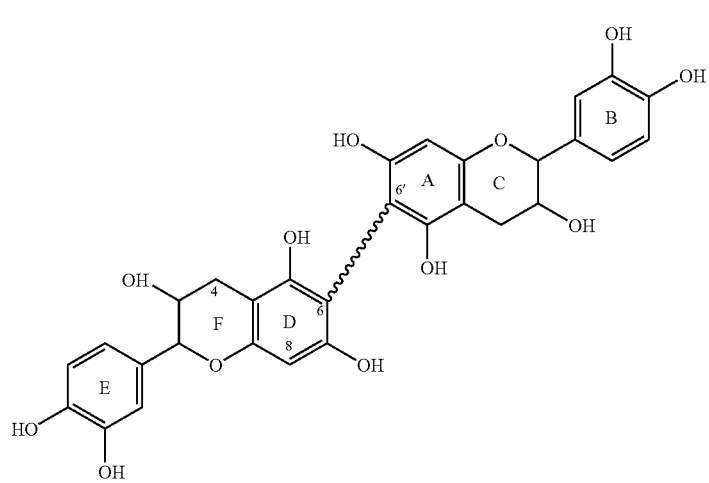

to Romanczyk et al. Such uses include the use as antineoplastic agents, anti-cancer agents, anti-tumor agents, antioxidants, DNA topoisomerase inhibitors, cyclo-oxygenase and lipoxygenase modulators, nitric oxide or nitric oxide synthase modulators, non-steriodal antinflammatory agents, apoptosis modulators, platelet aggregation modulators, blood or in vivo modulators, antimicrobials, and inhibitors of oxidative DNA damage.

EXAMPLES

In the following examples, (+)-catechin and (−)-epicatechin are exemplary procyanidin monomers used to demonstrate the methods of the invention and no limitation of the invention is implied. These monomers may be obtained from commercial sources or isolated and purified from natural sources such as from the seeds of *Theobroma cacao*, related species, the genus *Herrania* and their inter- and intra-genetic crosses. Unless specified otherwise, the purity of compounds prepared in the Examples were ~85% or better.

Example 1

Preparation of Tetra-O-benzyl-(+)-catechin

To a solution of (+)-catechin (580 mg, 2 mmol) in DMA (15 mL), benzyl bromide (960 μL, 4 eq) and $K_2CO_3$ (1.7 gm, 6 eq) were added and the mixture stirred at r.t. under argon for 48 hours. The mixture was then partitioned between ethyl acetate and water (50 mL each). The organic layer was washed with water (3×50 mL), then 50 mL saturated NaCl. Removal of the solvent gave a viscous residue from which the title compound was isolated by crystallization from 50 mL methylene chloride:methanol (9:1; v/v) to provide 880 mg of off-white crystals at a yield of 68%. $^1$H NMR (CDCl$_3$) $\delta_H$ 7.44-7.24 (20H, m, Ar—H), 7.0 (1H, s, H-2'), 6.94 (2H, s, H-5', H-6'), 6.25, 6.19 (2×1H, 2×d, J=2.0 Hz, H-6, H-8), 5.16 (4H, s, CH$_2$Ph), 5.0, 4.97 (2×2H, 2×s, CH$_2$Ph), 4.61 (1H, d, J=8.2 Hz, H-2), 3.98 (1H, m, H-3), 3.10 (1H, dd, J=16.5 Hz, H-4α), 2.63 (1H, dd, J=8.9, 16.5 Hz, H-4β).

Example 2

Preparation of Tetra-O-benzyl-(−)-epicatechin

The title compound was prepared in an identical manner to that set forth in Example 1 except that (−)-epicatechin was used in place of (+)-catechin to provide 893 mg of off-white crystals at a yield of 69%. $^1$H NMR (CDCl$_3$) $\delta_H$ 7.43-7.30 (20H, m, Ar—H) 7.13 (1H, s, H-2'), 6.96 (2H, s, H-5', H-6'), 6.26 (2H, m, H-6, H-8), 5.18, 5.16 (2×2H, s, CH$_2$Ph), 5.01, 4.99 (2×2H, 2×s, CH$_2$Ph), 4.90(1H, s, H-2), 4.19 (1H, bm, H-3), 2.45 (2H, m, H-4), 1.64 (1H, d, J=3.8 Hz, OH).

Example 3

Preparation of Pentaacetyl (−)-epicatechin 500 mg (−)-epicatechin (1.6 mmole) was dissolved in 5 mL cold (0° C.) dry pyridine. 2 mL of acetic anhydride was added, the solution stirred for 18 hours under an argon atmosphere. The solution was then partitioned between 50 mL ethyl acetate:50 mL 1N HCl and the organic layer washed 3×50 mL with 1N HCl, followed by 50 mL water and 50 mL saturated NaCl. The washed organic layer was dried over MgSO$_4$, filtered and dried to obtain a viscous oil which solidified upon addition of 100 mL hexane to provide 720 mg of product at a yield of 90%. $^1$H NMR (CDCl$_3$) $\delta_H$ 7.36 (1H, d, J=2 Hz, H-2'), 7.27 (1H, dd, J=2.0, 8.4 Hz, H-6'), 7.20 (1H, d, J=8.4 Hz, H-5'), 6.67(1H, d, J=2.3Hz, H-6, or H-8), 6.56 (1H, d, J=2.3 Hz, H-8 or H-6), 5.38 (1H, m, H-3), 5.11 (1H, bs, H-2), 2.98 (1H, dd, J=4.4, 17.8 Hz, H-4), 2.87 (1H, dd, J=2, 17.8 Hz, H-4), 2.299, 2.297, 2.295, 2.282, 1.920 (5×3H, 5×s, 5×COCH$_3$).

Example 4

Preparation of Pentaacetyl (+)-catechin

The title compound was prepared in an identical manner to that set forth in Example 3 except that (+)-catechin was used in place of (−)-epicatechin to provide 720 mg at a yield of 90%. $^1$H NMR (CDCl$_3$) $\delta_H$ 7.16 (1H, d, J=2 Hz, H-2'), 7.26 (1H, dd, J=2.0, 8.4 Hz, H-6'), 7.19 (1H, d, J=8.4 Hz, H-5 '), 6.66 (1H, d, J=2.3 Hz, H-6, or H-8), 6.59 (1H, d, J=2.3 Hz, H-8 or H-6), 5.25(1H, m, H-3), 5.15 (1H, d, J=6.1 Hz H-2), 2.87 (1H, dd, J=5.1, 16.8 Hz, H-4), 2.63 (1H, dd, J=6.4, 16.8Hz, H-4), 2.290, 2.286, 2.279, 2.051, 2.006 (5×3H, 5×s, 5×COCH$_3$).

Example 5

Preparation of Tetra-O-p-methoxybenzyl-3-acetyl-(−)-epicatechin

To a mixture of pentaacetyl (−)-epicatechin (50 mg, 0.2 mmol), p-methoxybenzyl chloride (69 mg, 4.4 eq), 60% NaH in mineral oil (10 mg, 4 eq) and DMF (5 mL), water (20 μL, 4 eq) was added at 0° C. dropwise over a period of 5 minutes. After stirring under argon for 12 hours at r.t., the reaction mixture was diluted with ethyl acetate (30 mL) and washed with water (50 mL) and 30 mL saturated NaCl. The organic layer was dried over MgSO$_4$ and the solvent evaporated to obtain a pale yellow oil from which the title compound was isolated by silica gel chromatography as a white solid, crystallized from hexane:methylene chloride (1:1, v/v); yield (50 mg, 70%). $^1$H NMR (CDCl$_3$) $\delta_H$ 7.35-7.29 (9H, m, Ar—H), 6.92-6.85 (10H, m, Ar—H), 6.26 (2H, bs, H-6, H-8)), 5.38 (1H, m, H-3), 5.06-6.85(8H, m, 4×CH$_2$), 4.92 (1H, s, H-2), 3.80 (12H, overlapping singlets, 4×OCH$_3$), 2.93 (2H, m, H-4), 1.85 (3H, s, OCOCH$_3$).

Example 6

Preparation of 4β-Acetoxy tetra-O-benzyl-(+)-catechin

Tetra-O-benzyl-(+)-catechin (300 mg, 0.46 mmole) and lead tetraacetate (304 mg, 1.5 eq) were combined in a round bottom flask and dried under vacuum for 30 min. Argon was introduced, followed by addition of benzene and glacial acetic acid (5 mL each). The initial yellow color faded on addition of acetic acid. The solution was stirred for 24 hours at r.t. and transferred to a separatory funnel. The mixture was washed with cold 1N NaOH (4×50 mL), followed by water (50 mL) and finally with saturated NaCl (50 mL). The organic layer was dried over Na$_2$SO$_4$ followed by removal of solvent to produce a brownish residue from which silica gel chromatography furnished the title compound by elution with hexane:ethyl acetate (7:3, v/v). The elute was evaporated to produce 210 mg, 66% of the title compound. $^1$H NMR (CDCl$_3$) $\delta_H$ 7.44-7.28 (20H, m, Ar—H), 7.08 (1H, s, H-2'), 7.01, 6.95 (2H, ABq, J=8.3 Hz, H-5'H-6'),6.41 (1H, d, J=3.6 Hz, H-4), 6.23, 6.15 (2×1H, 2×d, J=2.1 Hz, H-6, H-8), 5.16 (4H, s, CH$_2$Ph), 5.05, 4.97 (2×2H, 2×s, CH$_2$Ph), 4.83 (1H, d, J=10.3 Hz, H-2), 4.13 (1H, dd, J=3.6, 10.3 Hz, H-3), 2.23 (1H, bs, OH), 2.07 (3H, s, COCH$_3$).

Example 7

Preparation of 4β-Acetoxy tetra-O-benzyl-(−)-epicatechin

The title compound was prepared in an identical manner to that set forth in Example 6 except that 1.01 gm of tetra-O-benzyl-(−)-epicatechin (1.55 mmol) was used in place of tetra-O-benzyl-(+)-catechin to provide 62 mg, 59% product. $^1$H NMR (CDCl$_3$) δ$_H$ 7.44-7.24 (20H, m, Ar—H), 7.12 (1H, s, H-2'), 6.98, 6.95 (2H, ABq, J=8.3 Hz, H-5', H-6'), 6.25 (2H, s, H-6, H-8), 5.16 (4H, s, CH$_2$Ph), 6.10, (1H, d, J=2.5 Hz, H-4), 5.17, 5.16, 5.03 (4×2H, 4×s CH$_2$Ph), 4.97 (1H, s, H-2), 3.95(1H, m, H-3), 2.0 (3H, s, COCH$_3$).

Example 8

Preparation of 4β-Hydroxyl tetra-O-benzyl-(+)-catechin

To a solution of 4-acetoxy tetra-O-benzyl-(+)-catechin (692 mg, 1 mmol) in THF (9 mL) and methanol (1 mL), powdered KOH (168 mg, 3 eq) was added, and the solution stirred at r.t. for 2 hours. Saturated NH$_4$Cl (25 mL) was added and the solution extracted 2×25 mL with ethyl acetate. The organic layer was dried over Na$_2$SO$_4$ and the solvent evaporated to provide an off-white solid (650 mg, quantitative). $^1$H NMR (CDCl$_3$) δ$_H$ 7.45-7.28 (20H, m, Ar—H), 7.08 (1H, s, H-2'), 6.99, 6.95 (2H, ABq, J=8.3 Hz, H-5', H-6'), 6.26, 6.15 (2×1H, 2×d, J=2.1 Hz, H-6, H-8), 5.16 (4H, s, CH$_2$Ph), 5.06 (3H, m, H-4, CH$_2$Ph), 4.97 (2H, s, CH$_2$Ph), 4.85 (1H, d, J=9.9Hz, H-2), 3.95(1H, m, H-3), 2.75 (1H, bs, OH), 2.55 (1H, bs, OH).

Example 9

Preparation of 4β-Hydroxyl tetra-O-benzyl-(−)-epicatechin

The title compound was prepared in an identical manner set forth in Example 8, except that 4β-acetoxy tetra-O-benzyl-(−)-epicatechin was used in place of 4β-acetoxy tetra-O-benzyl-(+)-catechin to provide 287 mg, 86% product. $^1$H NMR (CDCl$_3$) δ$_H$ 7.45-7.31 (20H, m, Ar—H), 7.16 (1H, s, H-2'), 6.99, 6.95 (2H, ABq, J=8.3 Hz, H-5', H-6'), 6.29, 6.27 (2×1H, 2×d, J=2.1 Hz, H-6, H-8), 5.18(4H, s, CH$_2$Ph), 5.18 (4H, s, CH$_2$Ph), 5.07 (3H, m, H-4, CH$_2$Ph), 5.01 (2H, s, CH$_2$Ph), 4.92(1H, s, H-2), 3.98 (1H, dd, J=2.5, 5.7 Hz, H-3), 2.43 (1H, d, J=2.4 Hz, OH), 1.58 (1H, d, J=5.7 Hz, OH).

Example 10

Preparation of 4β-Methoxy tetra-O-benzyl-(+)-catechin

To a solution of 4-acetoxy tetra-O-benzyl-(+)-catechin (70 mg, 0.1 mmol) in methylene chloride (5 mL) and methanol (1 mL), LiBr (87 mg, 10 eq) was added and the solution refluxed for 4 hours. The mixture was then partitioned between methylene chloride and water (25 mL each). The organic layer was dried over Na$_2$SO$_4$, filtered and the solvent evaporated. The residue was subjected to silica gel chromatography to produce 54 mg, 80% of the title compound as pale yellow oil. $^1$H NMR (CDCl$_3$) δ$_H$ 7.42-7.27 (20H, m, Ar—H), 7.07 (1H, d, J=1.6 Hz, H-2'), 6.96 (2H, m, H-5', H-6'), 6.26(1H, d, J=2.2 Hz, H-6 or H-8), 6.15 (1H, d, J=2.2 Hz, H-8, H-6) 5.15 (4H, s, CH$_2$Ph), 5.02(2H, ABq, J=7.8 Hz, CH$_2$Ph), 4.97 (2H, s, CH$_2$Ph), 4.92 (1H, d, J=10.4 Hz, H-2), 4.72 (1H, d, J=3.5Hz, H-4), 3.85 (1H, dt, J=3.5, 9.2 Hz, H-3), 3.47 (3H, s, OCH$_3$).

Example 11

Preparation of Tetra-O-benzyl-(+)-catechin-(4α→8)-(−)-epicatechin

4β-Acetoxy tetra-O-benzyl-(+)-catechin (Example 6) (140 mg, 0.2 mmol), (−)-epicatechin (290 mg, 5 eq) and LiBr (87 mg, 5 eq) were dissolved in a mixture of THF and methylene chloride (5 mL each) and the solution refluxed for 24 hours after which the solution was partitioned between ethyl acetate and water (40 mL each). The organic layer was dried over Na$_2$SO$_4$ followed by evaporation of the solvent. The residue was resuspended in ethyl acetate and filtered to remove most of the (−)-epicatechin. The filtrate was evaporated and subjected to silica gel chromatography where methylene chloride:ethyl acetate (1:1, v/v) elute furnished 116 mg, 62% dimer as an off-white powder. For the NMR spectrum the Hs comprising the upper monomer of the dimer are designated A and the Hs comprising the lower monomer of the dimer are designated B. $^1$H NMR (CDCl$_3$: d$_4$-menthanol, 9:1) δ$_H$ 7.36-7.23 (20H, m, Ar—H), 7.02-6.74(5H, m, A-5', A-6', A-2', B-2', B-5'), 6.35 (1H, dd, J=1.7, 8.2 Hz, B-6'), 6.18-6.16 (2H, ABq, J=2.2 Hz, A-6, A-8), 5.86 (1H, s, B-6), 5.12 (5H, m, CH$_2$Ph, B-2), 4.90 (2H, s, CH$_2$Ph), 4.71 (1H, d, J=8.2 Hz, A-2), 4.59 (1H, d, J=10 Hz, CH$_2$Ph), 4.47 (1H, d, J=10 Hz, CH$_2$Ph), 4.29 (1H, dd, J=8.3, 8.3 Hz, A4), 3.80 (1H, m, H-3), 2.71 (1H, d, J=16.6 Hz, B-4), 2.53 (1H, dd, J=4.4, 16.6 Hz, B4); $^{13}$C NMR δ156.5, 156.0, 154.6, 154.0, 152.5, 151.6, 151.4, 151.2, 150.6, 147.0, 146.7, 141.7, 141.6, 141.5, 139.8, 134.8, 134.4, 134.2, 133.9, 129.3, 128.7, 126.2, 126.1, 126.0, 125.8, 125.5, 125.4, 125.2, 125.1, 125.0, 124.9, 119.8, 115.0, 112.6, 111.2, 106.1, 104.5, 96.5, 94.9, 93.0, 92.8, 79.9, 70.5, 69.1, 69.0, 67.8, 67.7, 63.9, 35.0, 25.5; IR (KBr, cm$^{-1}$) 3418, 3057, 3034, 2918, 1609, 1510, 1446, 1371, 1260, 1202, 1097, 806, 731, 696; MS (FAB, m/z) 939.6 (M+H)$^+$, 649.1, 607.0, 559.0, 459.8.

Example 12

Preparation of (+)-Catechin (4α→8)-(−)-epicatechin

Tetra-O-benzyl-(+)-catechin-(4α→8)-(−)-epicatechin prepared in Example 11 (50 mg) was dissolved in methanol (10 mL) and degassed by blowing argon for 10 min. 30% Palladium-charcoal (30 mg) was added and hydrogenolysis conducted at 45 psi for 3 hours. The solution was filtered through Celite which was washed with methanol. The combined filtrate and washings were evaporated and the residue was dissolved in water, then lyophilized to provide a quantitative yield of the dimer as an off-white solid. For the NMR spectrum the Hs comprising the upper monomer of the dimer are designated A and the Hs comprising the lower monomer of the dimer are designated B. $^1$H NMR (CDCl$_3$: d$_4$-menthanol, 9:1) δ$_H$ 7.21 (1H, bs, A-2'), 7.04 (1H, bs, B-2'), 6.95-6.75 (2H, m, A-5', B-5'), 6.62 (1H, m, A-6'), 6.45 (1H, m, B-6'), 6.20 (1H, m, B-6), 6.05 (1H, m, B-6), 5.89 (2H, m, A-6, A-8), 4.98 (1H, m, B-2,), 4.85 (1H, m, B-2), 4.42-4.25 (3H, m, A-4, A-3, A-2), 3.05-2.62 (2H, m, B-4).

Example 13

Preparation of 3-Acetyl-tetra-O-benzyl-(+)-catechin-(4α→8)-pentaacetyl-(−)-epicatechin Tetra-O-benzyl-(+)-catechin-(4α→8)-epicatechin prepared in Example 11 was acetylated with acetic anhydride in pyridine. 120 mg of tetra O-benzyl-(+)-catechin (4α→8)-(−)-epicatechin was dissolved in 2 mL of dry pyridine and 500 µL of acetic anhydride added. The reaction mixture was stirred under argon for 18 hours at r.t. The mixture was partitioned between ethyl acetate and 1N HCl (25 mL each). The organic layer was washed with 25 mL water, followed by 25 mL 5% sodium bicarbonate, followed by 25 mL saturated NaCl and the organic phase dried over $Na_2SO_4$. The product was purified by chromatography to provide 140 mg of the title compound at a yield of 91%. For the NMR spectrum the Hs comprising the upper monomer of the dimer are designated A and the Hs comprising the lower monomer of the dimer are designated B. $^1$H NMR (CDCl$_3$: d$_4$-methanol, 9:1) $\delta_H$ 7.40-7.29 (20H, m, Ar—H), 7.19-7.13 (5H, m, A-2', A-6', B-2', B-5', B-6'), 6.92 (1H, d, J=8.3 Hz, A-5'), 6.52 (1H, s, B-6), 6.21, 6.18 (2×1H, 2×d, J=2.3 Hz, A-6, A-8), 5.67 (1H, t, J=9.6, Hz, H-3), 5.14(3H, s, CH$_2$Ph, B-3), 5.0 (2H, s, CH$_2$Ph,), 4.98 (2H, s, CH$_2$Ph,) 4.84 (1H, d, J=9.1Hz, A-3), 4.75(1H, d, J=10.1 Hz, A-2), 4.58, 4.41 (2H, ABq, J=9.2 Hz, CH$_2$Ph), 2.64 (2H, m, B4), 2.29 (6H, s, COCH$_3$), 2.26 (3H, s, COCH$_3$), 2.26 (3H, s, COCH$_3$) 1.76 (3H, s, COCH$_3$), 1.74 (3H, s, COCH$_3$), 1.64 (3H, s, COCH$_3$); $^{13}$C NMR 169.6, 168.2, 168.0, 167.5, 158.0, 156.2, 153.2, 149.2, 148.7, 147.1, 146.2, 142.5, 142.0, 137.0, 136.8, 136.5, 136.2, 130.0, 129.8, 128.3, 128.2, 127.7, 127.6, 127.3, 127.1, 122.8, 121.6, 121.4, 114.9, 114.8, 110.2, 108.4, 106.0, 95.0, 94.6, 80.0, 75.5, 73.4, 71.4, 71.0, 70.5, 69.7, 66.5, 35.0, 26.2, 20.6, 20.5, 20.4, 20.3, 20.0; MS (FAB, m/z) 1192 (M+H)$^+$, 1131, 1039, 949, 841, 691.

Example 14

Preparation of 3-Acetyl-(+)-catechin (4α→8)-pentaacetyl-(−)-epicatechin

3-Acetyl-tetra-O-benzyl-(+)-catechin (4α→8)-pentaacetyl-(−)-epicatechin prepared in Example 13 was dissolved in degassed ethyl acetate-methanol (3 mL each) and hydrogenated with 30% palladium-charcoal at 45 psi for 4 hours. The solution was filtered through Celite and the solvent evaporated to provide a quantitative yield of the dimer as a pale yellow solid. For the NMR spectrum the Hs comprising the upper monomer of the dimer are designated A and the Hs comprising the lower monomer of the dimer are designated B. $^1$H NMR (CDCl$_3$: d$_4$-methanol, 9:1) $\delta_H$ 7.47, 6.98 (2×1H, bs, B-2'), 7.36, 6.98 (2×1H, 2×d, J=8.4, B-6'), 7.24, 7.16 (2×1H, 2×d, J=8.4Hz, B-5'), 6.89, 66.0(2× 1H, 2×bs, A-2'), 6.83, 6.79 (2×1H, ABq, J=8.4 Hz, A-5', A-6'), 6.66 (1H, d, J=8.4Hz, A-5'), 6.47 (1H, d, J=8.4 Hz, A-6'), 6.51, 6.45 (2×1H, 2×s, B-6), 5.97, 5.84 (2×1H, 2×d, J=2 Hz, A-6, A-8), 5.96 (2H, s, A-6, A-8), 5.71 (2H, m, A-3), 5.50, 5.17 (2×1H, 2×bs, B-3), 5.28 (2×1H, 2×bs, B-2), 5.0, 4.54 (2×1H, 2×d, J=8.9, 9.4 Hz, A-2), 4.74, 4.61 (2×1H, 2×d, J=9.9 Hz, A-4), 3.2,2.74 (2×2H, 2×m, B-4), 2.32, 2.29, 2.28, 2.26, 2.23, 2.01, 1.80, 1.77, 1.63 (s, COCH$_3$); $^{13}$C NMR 172.5, 172.0, 171.8, 171.5, 170.3, 170.2, 170.1, 170.0, 169.8, 169.2, 157.2, 157.1, 156.8, 154.8, 154.0, 149.2, 147.5, 146.0, 145.9, 145.6, 145.0, 143.0, 142.8, 137.5, 137.0, 129.8, 125.8, 124.9, 124.0, 123.0, 122.6, 121.8, 120.8, 120.2, 119.8, 115.9, 115.8, 115.5, 115.1, 110.8, 110.9, 109.5, 109.4, 105.0, 104.2, 98.0, 97.5, 96.8, 96.0, 81.0, 80.2, 79.0, 78.8, 78.6, 78.0, 75.0, 72.2, 68.1, 68.0, 37.5, 36.0, 26.5, 26.0, 20.7.

Example 15

Preparation of Tetra-O-benzyl-(−)-epicatechin-(4β→8)-(−)-epicatechin

4β-Acetoxy tetra-O-benzyl-(−)-epicatechin prepared by Example 7(70 mg. 0.1 mmol), (−)-epicatehin (145 mg, 5 eq) and LiBr (44 mg, 5 eq) were disolved in a mixture of THF and methylene chloride (3 mL each) and the solution refluxed for 24 hours under argon. The solution was partitioned between ethyl acetate and water (25 ml each) and the organic layer dried over $Na_2SO_4$. The solvent was evaporated and the residue resuspended in 25 ml ethyl acetate followed by filtration to remove most of the unreacted (−)-epicatechin. The filtrate was evaporated to a residue and the title compound isolated from silica gel chromatography by methylene chloride:ethyl acetate (1:1, v/v) elution. Evaporation of the eluate provided 56 mg (60%) of an off-white powder. $_1$NMR (CDCl$_3$:d$_4$menthanol, 9:1) $\delta_H$[No assignment]7.35-7.14 (20H, m), 6.92 (1H, bs), 6.82 (1H, s), 6.29 (1H, s) 6.18 (1H, s), 5.85 (1H, s), 5.01 (4H, s), 4.94 (2H, s), 4.93 (2H, s), 4.38 (1H, s), 3.93 (1H, s,) 2.85 (2H, s).

Example 16

Preparation of (−)-Epicatechin-(4β→8)-(−)-epicatcehin

Tetra-O-(−)epicatechin (4β→8)-(−)-epicatcchin prepared in Example 15 (40 mg, 0.043 mmol) was dissolved in 8 mL methanol and degassed by blowing argon for 10 min. To the solution, 25 mg of 30% palladium-charcoal was added and the mixture hydrogenolyzed at 45 psi for 3 hours. The solution was filtered through Celite followed by washing with 25 mL methanol. The combined filtrate and washing were evaporated and the residue dissolved in water. Lyophilization provided 23 mg of an off-white powder. HPLC analysis revealed the presence of 18% monomer, 45% dimer, 25% trimer and 8% tetramer.

Example 17

Preparation of Tetra-O-benzyl-(+)-catechin-(4α→8)-(+)-catechin

4β-Acetoxy tetra-O-benzyl-(+)-catechin prepared by Example 6 (70 mg. 0.1 mmol), (+)-catechin (145 mg, 5 eq) and LiBr (44 mg, 5 eq) were dissolved in a mixture of THF and methylene chloride (3 mL each) and the solution refluxed for 24 hours under argon. The solution was partitioned between ethyl acetate and water (25 mL each) and the organic phase dried over $Na_2SO_4$. Following evaporation, the residue was resuspended in ethyl acetate (25 mL) and filtered to remove most of the unreacted (+)-catechin. After evaporation, the residue was subjected to silica gel chromatography where elution with methylene chloride:ethyl acetate (1:1, v/v) provided an off-white powder (81 mg, 68%) after evaporation. $^1$H NMR (CDCl$_3$:d$_4$-methanol, 9:1) $\delta_H$ 7.39-7.06 (20H, m), 6.84-6.68 (5H, m), 6.47(1H, d, J=7.9 Hz), 6.32-5.98 (4H, m), 5.00-4.33 (11H, m), 3.58 (1H, m), 2.98 (1H, m), 2.35 (1H, m); IR (KBr, cm$^{-1}$) 3441, 3057, 3034, 2918, 1609, 1542, 1510, 1371, 1266, 1097, 812, 737, 696; MS (APCI, m/z) 938 (M–H), 920, 848, 816, 696, 607, 558.

Example 18

Preparation of 3-Acetyl-tetra-O-benzyl-(+)-catechin-(4α→8)-3-acetyl tetra O-benzyl-(–)-epicatechin 3-Acetyl tetra-O-benzyl-(+)-catechin (4α→8)-pentaacetyl-(–)-epicatechin prepared by Example 13 (119 mg, 0.1 mmol) was added to dry DMF (4 mL) at 0° C., followed by NaH (29 mg, 4.2 eq), followed by benzyl bromide (54 µL, 4.5 eq). Water (8 µL, 4 eq) was added slowly over 2 minutes and the mixture was stirred for 24 hours at r.t. The solution was partitioned between ethyl acetate and water (25 mL each) and the organic phase was dried over $MgSO_4$. Following evaporation, the residue was subjected to silica gel chromatography where elution with 20% ethyl acetate in hexane provided 105 mg (90%) of the title compound after evaporation. For the NMR spectrum the Hs comprising the upper monomer of the dimer are designated A and the Hs comprising the lower monomer of the dimer are designated B. $^1$H NMR ($CDCl_3$ $d_4$-methanol, 9:1) $\delta_H$ 7.45-7.24 (40H, m, Ar—H), 6.90-6.78 (6H, m, A-2', A-5', A-6', B-2', B-5', B-6'), 6.22 (2H, m, A-6, A-8), 6.21 (1H, s, B-6), 5.92 (1H, m, A-3), 5.21-4.40 (20H, complex, $CH_2Ph$, A-2, A-4, B-2, B-3), 2.70 (2H, m, B-4), 1.67 (6H, s, $CH_2Ph$,), $COCH_3$).

Example 19

Preparation of Tetra-O-benzyl-(+)-catechin-(4α→8)-(+)-tetra-O-benzyl-(–)-epicatechin To a solution of 3-acetyl tetra-O-benzyl-(+)-catechin-(4α→8)-3 acetyl tetra-O-benzyl-(–)-epicatechin prepared in Example 18 (40 mg, 0.03 mmol) in the THF (2 mL) and methanol (200 µL), powdered KOH (5 mg, 3 eq) was added and the solution stirred at r.t. for 18 hours under argon. The reaction mixture was partitioned between ethyl acetate and saturated $NH_4Cl$ (25 mL each). The organic layer was dried over $MgSO_4$ and the solvent evaporated. The residue was then subjected to silica gel chromatography where elution with 20% ethyl acetate in methylene chloride provided the title compound (31 mg, 82.5%) as a colorless oil after evaporation of the solvent. For the NMR spectrum the Hs comprising the upper monomer of the dimer are designated A and the Hs comprising the lower monomer of the dimer are designated B. $^1$H NMR ($CDCl_3$ $d_4$-methanol, 9:1) $\delta_H$ 7.41-7.13 (40H, m, Ar—H), 6.97-6.79 (6H, complex, A-2', A-5', A-6', B-2', B-5', B-6'), 6.22 (1H, s, B-6), 6.20, 6.12 (2×1H, 2×d, J=2.4 Hz, A-6, A-8), 5.18-4.51 (19H, $CH_2Ph$, A-2, A-4, -2), 4.28 (1H, m, A-3), 3.85 (1H, m, B-3), 2.95 (1H, d, J=16 Hz, B4), 2.60 (1H, dd, J=5, 16 Hz, B4).

Example 20

Preparation of Tetra-O-benzyl-(+) catechin-(4α→8)-3-acetyl-(+)-catechin-(4α→8)-pentaacetyl (–)-epicatechin To a solution of 3-acetyl-(+)-catechin-(4α→)-pentaacetyl-(–)-epicatechin prepared by Example 14 (100 mg, 0.068 mmol) and 4βacetoxy tetra-O-benzyl-(+)-catechin prepared by Example 6 (334 mg, 2 eq) in THF (7 mL) and methylene chloride (7 mL), 161 mg of LiI was added. The solution was refluxed for 24 hours, followed by partition between ethyl acetate and water (25 mL each). The organic phase was dried over $Na_2SO_4$, filtered and the solvent evaporated. The residue was subjected to silica gel chromatography where elution with ethyl acetate-niethylene chloride (1:1, v/v) provided a brownish white solid (100 mg, 28%) after the evaporation of the solvent. MS (FAB, m/z) 1482 (M+H)$^+$, 1148, 1042, 962, 920, 650.

Example 21

Preparation of Tetra-O-benzyl-(+)-catechin -(4α→8)-pentaacetyl-(+)-epicatechin-(4α→8)-pentaacetyl (–)-epicatechin Tetra-O-benzyl-(+) catechin-(4α→8)-3-acetyl-(+)-catechin-(4α→8)-pentaacetyl (–)-epicatechin prepared by Example 20 (100 mg, 0.068 mmol) was stirred in dry pyridine (2 mL) and acetic anhydride (1 ml) under argon for 24 hours. The solution was then partitioned between 1 N HCl and ethyl acetate (25 mL each), the organic layer was washed with 5% $NaHCO_3$, saturated NaCl and dried over $MgSO_4$. Evaporation of the solvent provided an oily residue which was subjected to silica gel chromatography where elation with 10% ethyl acetate in methylene chloride provided a white powder (70 mg, 61%) after evaporation of the solvent.

Example 22

Preparation of 3 Acetyl-(+)-catechin -(4α→8) -pentaacetyl-(+)-catechin-(4α→8)-pentaacetyl (–)-epicatechin Tetra-O-benzyl- (+)-catechin-(4α→8)-pentaacetyl-(+)-catechin-(4α→8)-pentaacetyl (–)-epicatechin prepared in Example 21 (50 mg) was dissolved in degassed ethyl acetate-methanol (3 mL each) and hydrogenolysed for 4 hours in the presence of 30% palladium-charcoal (30 mg) at 45 psi. Removal of the catalyst via filtration through Celite and evaporation provided the title compound as a pale brown powder (35 mg, 91%).

Example 23

Tetra-O-benzyl-(+)-catechin-(4α→8)-3-acetyl-(+)-catechin-(4α→8)-pentaacetyl-(+)-catechin-(4α→8)-pentaacetyl (–)-epicatechin To a solution of 3-acetyl-(+)-catechin-(4α→8)-pentaacetyl-(+)-catechin-(4α→8)-pentaacetyl (–)-epicatechin prepared by Example 22 (30 mg, 0.0226 mmol) and 4β-acetoxy tetra-O-benzyl-(+)-catechin prepared by Example 6 (31 mg, 2 eq) in THF and methylene chloride (2 mL each), LiI (16 mg, 5 eq) was added and the solution refluxed for 24 hours. The solution was partitioned between ethyl acetate and water (25 mL each) and the organic layer dried over $MgSO_4$, filtered and the solvent evaporated. The residue was subjected to silica gel chromatography where elution with 10% methanol in methylene chloride provided a brownish-white solid (20 mg, 45%) after evaporation of the solvent. MS (FAB, m/z) 1978 (M+H)$^+$, 1934 (M$^+$-$COCH_3$), 1571 (M$^+$-$COCH_3$, –3×$CH_2Ph$), 1646, 1430, 1373, 1330, 1269.

Example 24

Preparation of Tetra-O-benzyl-(+)-catechin-(4α→8)-(−)-epicatechin-(6→4α)-tetra-O-benzyl-(+)-catechin To a solution of tetra-O-benzyl-(+)-catechin-(4α→8)-(−)-epicatechin prepared by Example 11 (69 mg, 0.074 mmol) and 4β-acetoxy tetra-O-benzyl-(+)-catechin prepared by Example 6 (51 mg, 0.074 mmol) in methylene chloride and THF (5 mL each), LiBr (65 mg, 10 eq) was added and the mixture refluxed for 24 hours. The solution was partitioned between ethyl acetate and water (25 mL each) and the organic layer dried over $MgSO_4$. The solvent was evaporated and the residue subjected to silica gel chromatography where elution with ethyl acetate-methylene chloride (1:1, v/v) provided a white powder (35 mg, 30%) after evaporation of the solvent. MS (FAB, m/z) 1588 (M+H)$^+$, 1255, 772, 648, 607, 560.

Example 25

Preparation of 8-Bromo tetra-O-benzyl-(−)-epicatechin

To a solution of tetra-O-benzyl-(−)-epicatechin (Example 2) (65 mg, 0.1 mmol) in methylene chloride (2 mL), N-bromosuccinimide (18 mg, 0.1 mmol) was added and the solution stirred under argon for 10 min. The mixture was filtered through silica gel followed by elution with 20 mL ethyl acetate:methylene chloride (1:1, v/v). The combined filtrate and eluant were evaporated. The residue was subjected to silica gel chromatography where elution with methylene chloride provided the title compound as shiny pinkish-white crystals (66 mg, 90%) after evaporation of the solvent. $^1$H NMR (CDCl$_3$) $\delta_H$, 7.45-7.21 (21H, m, Ar—H), 7.01 (1H, dd, J=1.4 8.3 Hz, H-6'), 6.96(1H, d, J=8.3Hz, H-5'), 6.23 (2H, s, H-6), 5.38 (1H, m, H-3), 5.21, 5.18, 5.10, 4.97 (4×2H, 4×s, 4×CH$_2$), 5.01(1H, s, H-2), 4.3 (1H, m, H-3), 3.03 (1H, dd, J=1.9, 17.4 Hz, H-4), 2.89 (1H, dd, J=4., 17.4Hz, H-4), 1.55 (1H, d, J=4.8 Hz, OH).

Example 26

Preparation of 8-Bromo penta-O-benzyl-(−)-epicatechin

To a solution of pentabenzyl-(−)-epicatechin (55 mg, 0.074 mmol) in methylene chloride (2 mL) at 0° C., N-bromosuccinamide (14 mg, 1 eq) was added and the solution stirred at r.t. for 30 min. The solution was passed through a 25 mm dia. column of silica gel (7 gm) which was eluted with methylene chloride (30 mL). The combined filtrate and eluant were evaporated to provide the title compound as a white foam (50 mg, 82.5%) after evaporation of the solvent. $^1$H NMR (CDCl$_3$) $\delta_H$, 7.43-6.90 (28H, m, Ar—H), 6.21 (1H, s, H-6), 5.17 (2H, s, CH$_2$), 5.09 (5H, s, 2×CH$_2$, H-2), 4.96(2, s, CH$_2$), 4.37, 4.27 (2H, AB, J=12.6 Hz, 3-OCH$_2$), 3.95 (1H, m, H-3), 2.94 (1H, dd, J=3.6, 17.1 Hz, H-4), 2.78 (1H, dd, J=4.4, 17.1 Hz, H-4).

Example 27

Preparation of 8-bromo 4β-acetoxy pentabenzyl-(−)-epicatechin

To a mixture of 8-bromo pentabenzyl-(−)-epicatechin (Example 26) (59 mg, 0.072 mmol) and lead tetraacetate (48 mg, 1.5 eq) under argon, benzene (2 mL) was added, followed by 2 mL acetic acid, and the mixture stirred for 60 hours at r.t. The solution was partitioned between ethyl acetate and water (50 mL each). The organic layer was washed with 1N NaOH (2×50 mL), followed by water (50 mL), saturated NaCl (50 mL), and was dried over Na$_2$SO$_4$. The solution was filtered and evaporated to provide an oily residue which was subjected to silica gel chromatography where elution with 20% ethyl acetate in hexane provided the title compound as a white foam (38 mg, 60%) after evaporation. $^1$H NMR (CDCl$_3$) $\delta_H$ 7.46-6.85 (28H, m, Ar—H), 6.25 (1H, s, H-6), 6.18(1H, d, J=2.3 Hz, H-4), 5.20, 5.13, 5.02 (4×2H, 4×s, 4×CH$_2$), 4.99 (1H, s, H-2), 4.51, 4.33 (2H, AB, J=12.3) Hz, 3-OCH$_3$), 3.65 (1H, m, H-3), 2.0 (2H, s, OCOCH$_3$).

Example 28

Determination of Absolute Configuration 8-bromo tetra-O-benzyl-(−)-epicatechin Crystals of 8-bromo tetra-O-benzyl-(−)-epicatechin were mounted on glass fibers and placed in a cold N$_2$ stream at −44° C. on a Siemens SMART CCD X-ray diffractometer. In general, the crystals diffracted poorly, with few or no high-angle reflections and with weak intensities overall. The first three crystals did not diffract well enough to measure the unit cell even at longer than usual exposure times. The fourth diffracted well enough to refine a unit cell using fifteen reflections. Data were collected on this crystal using fifty second exposures for over two thousand frames to approximately cover the diffraction sphere using Mo radiation.

The unit cell volume indicated two molecules in the unit cell. Although one cell angle was clearly 90° and one was clearly different from 90° (92.6°), the third angle differed from 90° by 0.1° which is a larger error than usual for a monoclinic cell. However, examination of possible systematic absences showed an apparent 2$_1$ axis consistent with the monoclinic space group P2$_1$ appropriate for a chiral compound. Subsequent successful structure solution and refinement in P2$_1$ supported that choice. The structure was solved by direct methods using the SHELX package (Sheldrick, G. M. SHELXTL *Structure Determination Software Programs*: Siemens Analytical X-ray Instruments Inc. Madison, Wis., 1990) of programs. Hydrogen atoms were placed in fixed, calculated positions. Phenyl rings in benzyl groups were refined isotropically as rigid groups. No corrections were made for absorption or extinction. The following table lists the crystal data.

TABLE

Crystal Data and Structure Refinement for 8-bromo tetra-O-benzyl-(−)-epicatechin

| | |
|---|---|
| Empirical Formula | $C_{43}H_{37}BrO_6$ |
| Formula Weight | 729.64 |
| Temperature | 229(2)° K |
| Wavelength | 0.71073 A° |
| Crystal System | Monolinic |
| Space Group | P2$_1$ |

TABLE-continued

Crystal Data and Structure Refinement for 8-bromo tetra-O-benzyl-(−)-epicatechin

| | |
|---|---|
| Unit Cell Dimensions | a = 15.9122(8) A°    alpha = 90° |
| | b = 4.8125(3) A°    beta = 92.6390(10)° |
| | c = 22.4772(13) A°    gamma = 90° |
| Volume, z | 1719.42(17) A$°^3$, 2 |
| Density (calculated) | 1.409 Mg/m$^3$ |
| Absorption coefficient | 1.246 mm$^{-1}$ |
| F(000) | 756 |
| Crystal Size | 0.45 × 0.04 × 0.04 mm |
| θ range for data collection | 1.28 to 23.44° |
| Limiting Indices | −17 ≦ h ≦ 17, −5 ≦ k ≦ 5, −24 ≦ l ≦ 24 |
| Reflections collected | 13371 |
| Independent reflections | 4868 (R$_{int}$ = 0.2246) |
| Completeness to θ = 23.44° | 99.2% |
| Absorption correction | None |
| Refinement method | Full matrix least squares on F$^2$ |
| Data/Restraints/Parameters | 4868/1/274 |
| Goodness of fit on F$^2$ | 1,091 |
| R indices (all) | R1 = 0.2263, wR2 = 0.4749 |
| Final R indices [I > 2σ (I)] | R1 = 0.1515, wR2 = 0.3875 |
| Absolute structure parameter | 0.00(5) |
| Largest diff. peak and hole | 1.857 and −1,268 eA$°^{-3}$ |

The assignment of the correct absolute configuration was tested by calculation of the Flack 'x' parameter. This parameter was indistinguishable from zero, indicating the correct configuration was assigned. A test refinement of the inverted configuration resulted in a Flack 'x' parameter value of 0.95(5) and a significant increase in the R factors, both indicating that the assignment was correct.

Example 29

Preparation of (8↔8), (8↔6), and (6↔6) Linked Procyanidin Oligomers

The steps described in this invention can be extended to provide procyanidin oligomers comprising (8↔8), (8↔6), (6↔6) interflavan linkages. These compounds are obtained from 6-bromo- and/or 8-bromo-(monomer) intermediates. Coupling of these brominated monomers with organotin derivatives by a Stille reaction in the presence of a palladium$_{(o)}$ catalyst leads to the desired oligomeric linkage. (Stille, J. K., *Agnew, Chem. Internal. Ed. Engl.*, 25, 508-524 (1986)).

For instance, 8-bromo pentabenzyl-(−)-epicatechin prepared by Example 26 reacted with hexaabutyl distannane to provide the alkyl stannane of pentabenzyl (−)-epicatechin. Coupling of this stannnane with another 8-bromo pentabenzyl (−)-epicatechin in the presence of tetrakis (triphenyl phosphine) palladium$_{(o)}$ in benzene provides the decabenzyl-(−)-epicatechin dimer with an (8→8) linkage. Deprotecting with H$_2$/Pd provides the (−)-epicatechin-(8↔8)-(−) -epicatechin in free phenolic form.

Similarly, procyanidin oligomers comprising (8↔6) or (6↔6) linkages can be synthesized using the appropriate 6-bromo- or 8-bromo-(monomer) derivatives. Further, coupling of 8-bromo- or 6-bromo- dimers, trimers and higher oligomers can provide "even" numbered procyanidin oligomers comprising (8↔8), (8↔6), and (6↔6) linkages.

Still further, coupling of blocked monomers used to prepare (4→6) linked oligomers as described in the invention can be used in the Stille reaction to provide novel procyanidin oligomers comprising combinations of the (4→6) and (4→8) linked oligomers with (8↔8), (8↔6), and (6↔6) linkages. By way of example, the following structure illustrates and (8↔8) and (4↔8) linked procyanidin trimer.

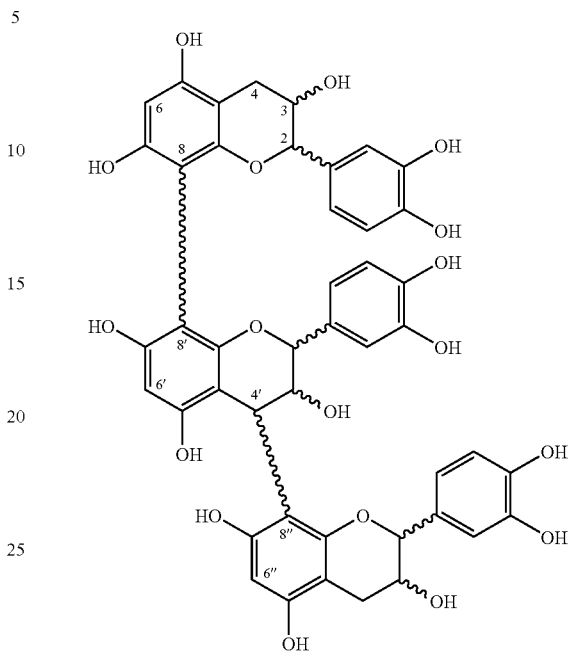

What is claimed is:

1. A process for preparing a partially protected procyanidin dimer which comprises the steps of:
   (a) protecting each phenolic hydroxyl group of an epicatechin or a catechin monomer;
   (b) activating the monomer from step (a) by introducing an acyloxy group at the C-4 position; and
   (c) catalytically coupling the monomer from step (b) with an unprotected epicatechin or an unprotected catechin monomer to form a partially protected procyanidin dimer where the top mer is protected and where the bottom mer is unprotected.

2. The process of claim 1, wherein the protecting groups are benzyl groups and wherein the protecting step is carried out with benzyl bromide in dimethyl formamide or dimethyl acetamide.

3. The process of claim 1, wherein the protecting groups are p-methoxybenzyl groups and the protecting step is carried out with p-methoxybenzyl chloride in dimethyl formamide.

4. The process of claim 2, wherein the protecting step is carried out in the presence of potassium carbonate or potassium iodide.

5. The process of claim 1, wherein the activating step is carried out using as an oxidizing agent a lead salt selected from the group consisting of lead acetate, lead formate, and lead propionate in a solvent selected from the group consisting of benzene, toluene, chlorobenzene, cyclohexane, heptane, carbon tetrachloride, and mixtures thereof.

6. The process of claim 5, wherein the lead acetate is used in combination with acetic acid; wherein the lead formate is used in combination with formic acid; wherein the lead propionate is used in combination with propionic acid; and wherein the solvent in the activating step is benzene-acetic acid.

7. The process of claim 1, wherein the catalyst used in the coupling step is a Lewis acid selected from the group consisting of lithium bromide and lithium iodide.

8. A process for preparing a linear procyanidin oligomer having 4→8 linkages, which process comprises the steps of:
   (a) preparing a partially protected 4→8 procyanidin dimer where the phenolic hydroxyl groups of the top mer are protected with removable protecting groups which do not deactivate the protected mer and where the phenolic hydroxyl groups of the bottom are unprotected;
   (b) masking the dimer of step (a) with removable masking groups which deactivate the bottom mer to form a dimer where the phenolic hydroxyl groups of the top mer are protected, where the phenolic hydroxyl groups of the bottom mer are masked, and where the hydroxyl groups at the C-3 positions of both mers are masked;
   (c) deprotecting the dimer of step (b) to form a dimer where the phenolic hydroxyl groups of the top mer are unprotected, where the phenolic hydroxyl groups of the bottom mer are masked, and where the hydroxyl groups at the C-3 positions of both mers are masked;
   (d) catalytically coupling the dimer of step (c) with a protected catechin monomer or a protected epicatechin monomer having an acyloxy activating group at the C-4 position to form a 4→8 trimer where the phenolic hydroxyl groups of the top mer are protected, where the phenolic hydroxyl groups of the middle mer are unprotected, where the phenolic hydroxyl groups of the bottom mer are masked, and where the hydroxyl groups at C-3 positions of the middle and the bottom mers are masked.

9. The process of claim 8, further comprising the step(s) of demasking and/or deprotecting the trimer of step (d).

10. The process of claim 8, which process further comprises the steps of:
   (e) masking the trimer of step (d) to form a trimer where the phenolic hydroxyl groups of the top mer are protected, where the phenolic hydroxyl groups of the middle and bottom mers are masked, and where the hydroxyl groups at the C-3 positions of all the mers are masked;
   (f) deprotecting the trimer of step (e) to form a trimer where the phenolic hydroxyl groups of the top mer are unprotected, where the phenolic hydroxyl groups of the middle and bottom mers are masked, and where the hydroxyl groups at the C-3 positions of all the mers are masked; and
   (g) catalytically coupling the trimer of step (f) with a protected catechin monomer or a protected epicatechin monomer having an acyloxy activating group at the C-4 position to form a 4→8 tetramer where the phenolic hydroxyl groups of the top mer are protected, where the phenolic hydroxyl groups of the middle mers and the bottom mer are masked, and where the hydroxyl groups at the C-3 positions of the middle mers and the bottom mer are masked; and
   (h) optionally repeating the masking, deprotecting, and coupling steps to form a higher oligomer.

11. The process of claim 10, further comprising the step(s) of demasking and/or deprotecting the tetramer of step (g) or higher oligomer of step (h).

12. The process of claim 10, wherein the higher oligomers include pentamers through dodecamers.

13. The process of claim 10, wherein the higher oligomers are the pentamers.

\* \* \* \* \*